(12) United States Patent
Patel

(10) Patent No.: US 11,833,347 B2
(45) Date of Patent: Dec. 5, 2023

(54) METHOD AND DEVICE FOR DEEP BRAIN STIMULATION

(71) Applicant: Bioinduction Limited, Bristol (GB)

(72) Inventor: Nikunj Kantilal Patel, Bristol (GB)

(73) Assignee: Bioinduction Limited

(*) Notice: Subject to any disclaimer, the term of this patent is extended or adjusted under 35 U.S.C. 154(b) by 106 days.

(21) Appl. No.: 17/025,149

(22) Filed: Sep. 18, 2020

(65) Prior Publication Data

US 2021/0085962 A1 Mar. 25, 2021

(30) Foreign Application Priority Data

Sep. 19, 2019 (GB) ...................... 1913489

(51) Int. Cl.
*A61N 1/36* (2006.01)
*A61N 1/372* (2006.01)
*A61N 1/05* (2006.01)

(52) U.S. Cl.
CPC ....... *A61N 1/0534* (2013.01); *A61N 1/36002* (2017.08); *A61N 1/36064* (2013.01); *A61N 1/36067* (2013.01); *A61N 1/36085* (2013.01); *A61N 1/36089* (2013.01); *A61N 1/36096* (2013.01); *A61N 1/372* (2013.01)

(58) Field of Classification Search
CPC ................ A61N 1/053; A61N 1/36002; A61N 1/36064; A61N 1/36067; A61N 1/36085; A61N 1/36089; A61N 1/36096; A61N 1/372
See application file for complete search history.

(56) References Cited

U.S. PATENT DOCUMENTS

| | | | |
|---|---|---|---|
| 10,118,038 B2* | 11/2018 | De Ridder | A61N 1/36178 |
| 2005/0021103 A1 | 1/2005 | DiLorenzo | |
| 2006/0293720 A1 | 12/2006 | DiLorenzo | |
| 2011/0046693 A1 | 2/2011 | Lee et al. | |
| 2016/0030666 A1 | 2/2016 | Lozano et al. | |
| 2016/0367809 A1 | 12/2016 | Patel et al. | |
| 2017/0151436 A1* | 6/2017 | Flaherty | A61N 7/00 |
| 2018/0236221 A1 | 8/2018 | Opie et al. | |
| 2019/0060634 A1 | 2/2019 | Skubitz et al. | |

FOREIGN PATENT DOCUMENTS

WO WO-2007007058 A1 * 1/2007 ......... A61N 1/36114

OTHER PUBLICATIONS

L. Mendelevitch, Extended European Search Report, 7 pages, dated Feb. 16, 2021, European Patent Office, Munich Germany.

* cited by examiner

*Primary Examiner* — William J Levicky
(74) *Attorney, Agent, or Firm* — McGarry Bair PC

(57) ABSTRACT

A method of treatment performed on a subject's brain includes a step of applying one or more neuromodulation signals to the lateral habenula and the posterior commissure.

13 Claims, 14 Drawing Sheets

PART SECTION A-A

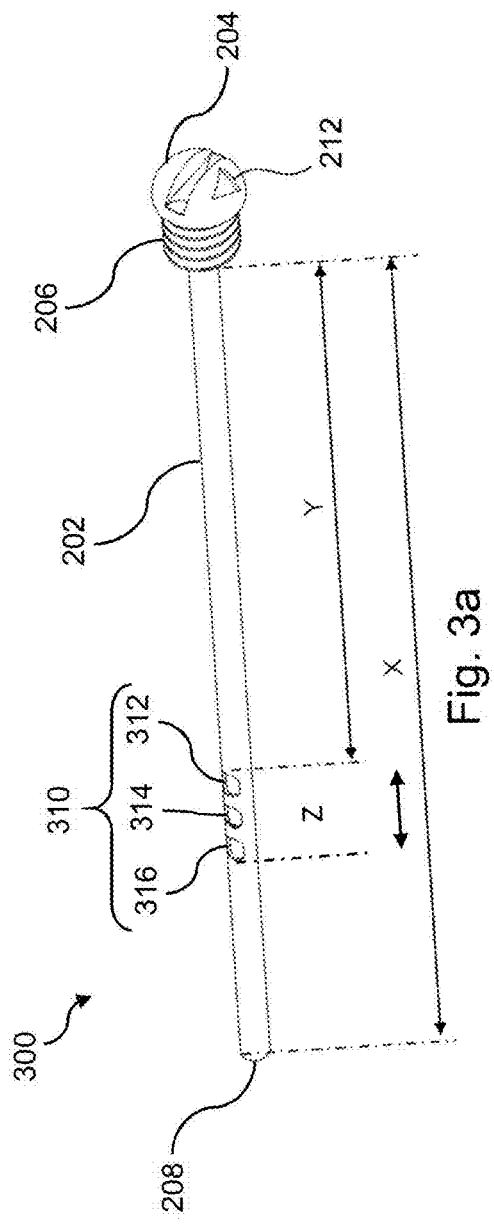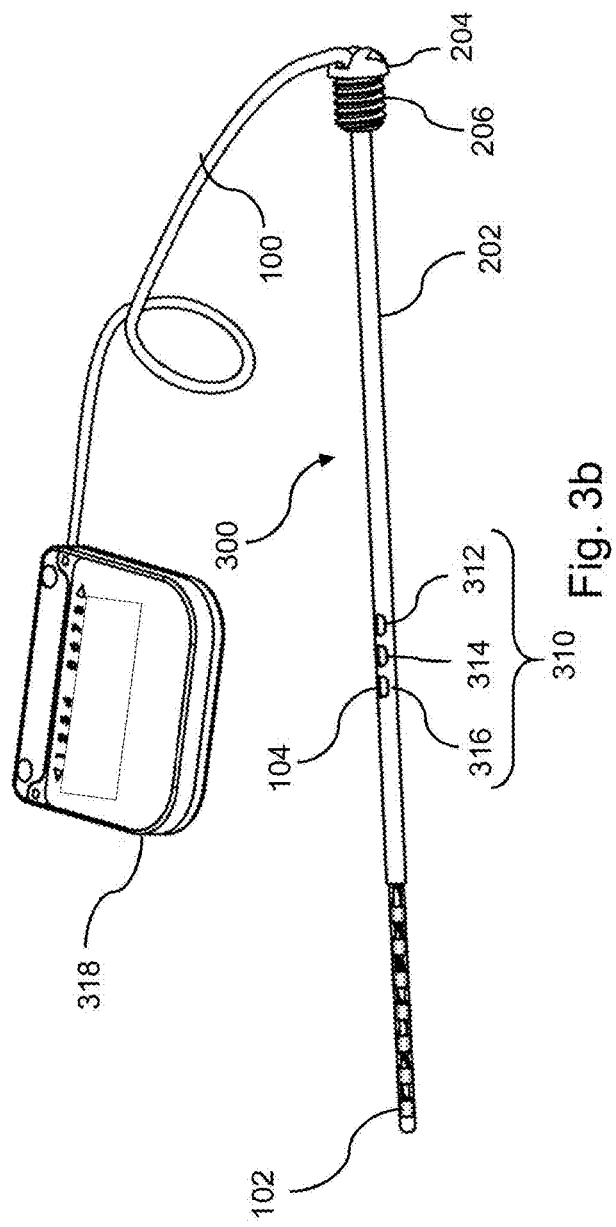

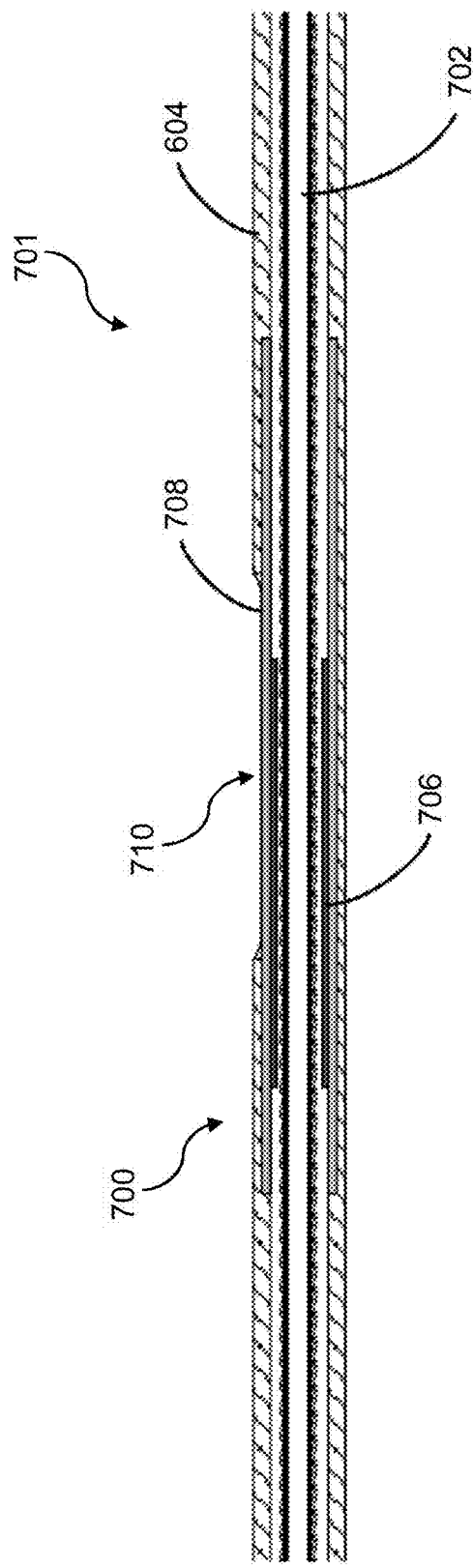
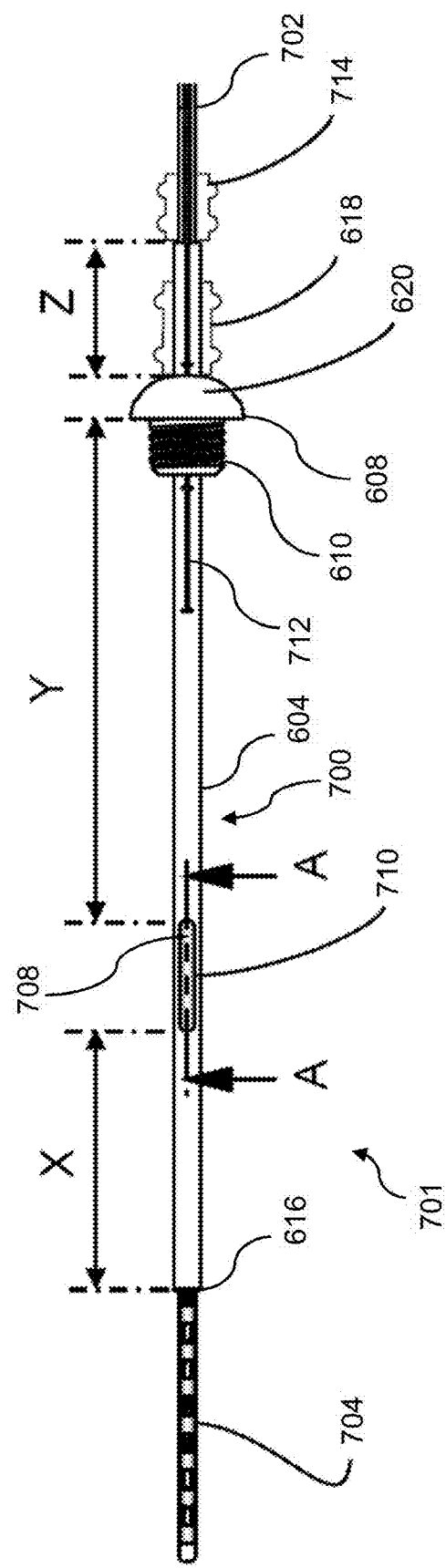
Fig. 7a
Fig. 7b

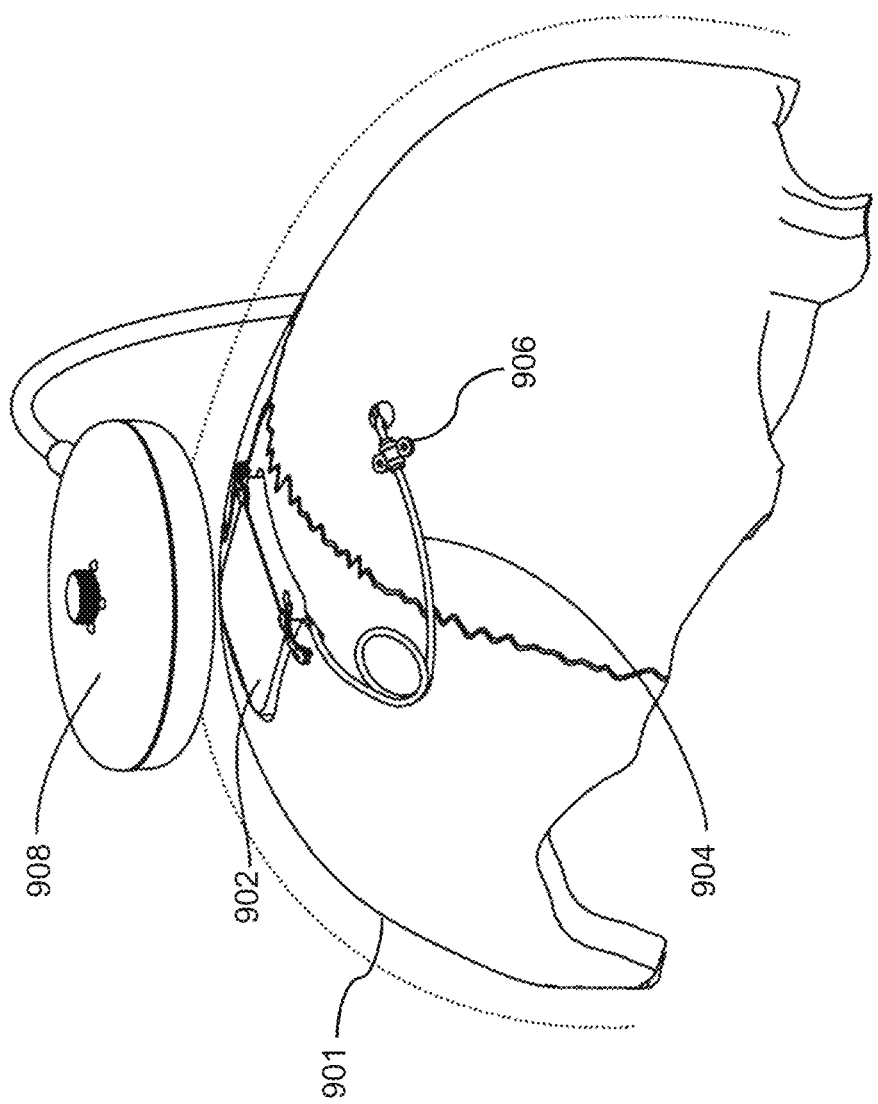

PART SECTION A-A

METHOD AND DEVICE FOR DEEP BRAIN STIMULATION

CROSS-REFERENCE TO RELATED APPLICATION

This application claims the benefit of British Application 1913489.9, filed on Sep. 19, 2019, and is incorporated herein in its entirety.

FIELD OF THE INVENTION

The present invention relates to a method and device for deep brain stimulation (DBS).

BACKGROUND TO THE INVENTION

Deep brain stimulation (DBS) is a neurosurgical procedure introduced in 1987 involving the implantation of electrodes to specific targets in the brain. A medical device known as a neurostimulator (sometimes referred to as a "brain pacemaker") is used to apply neurostimulation signals in the form of electrical impulses to the targets in the brain, via the electrodes, in order to alter brain circuits for the treatment of movement and neuropsychiatric disorders.

The technique is currently used to target the brain circuit involved in Parkinson's disease, dystonia and tremors, where it has been shown to be highly effective in controlling symptoms. Deep brain stimulation in select brain regions has also provided therapeutic benefits for otherwise treatment resistant disorders such as chronic pain, major depression, addiction, epilepsy, Tourette's disease and obsessive-compulsive disorder.

Despite the long history of DBS, its underlying principles and mechanisms remain unclear. It is widely thought that the electrical stimulus controls the excitability of neurons within close proximity of the implanted electrodes. Stimulus frequency is broadly used to excite (e.g. less than 50 hertz) or inhibit (e.g. greater than 100 hertz) neurons; the stimulus amplitude and pulse width are used to provide control of the amount of charge applied to reach and empirically define thresholds. Threshold response is also determined by the physical proximity of the electrode contacts to the brain target of interest.

Typically, the electrodes used for DBS are in the form of either circumferential (e.g. cylindrical) or directional contacts distributed along a lead, which is connected to an implantable pulse generator (IPG). This may enable either a monopolar stimulation configuration (with a case of the IPG acting as anode), or a bipolar stimulation configuration (between contacts).

In US 2016/0367809 A1, which is incorporated herein by reference, the inventors disclosed a method of treatment by neurostimulation of the periaqueductal gray (PAG) to increase brain perfusion, thereby enabling treatment of a range of conditions associated with compromised cerebral blood flow. US 2016/0367809 A1 also describes methods of treatment involving combined neurostimulation of the PAG and the dorsomedial nucleus of the thalamus.

SUMMARY OF THE INVENTION

The present invention builds on the inventors' work in US 2016/0367809 A1, and is based on the finding that combined neurostimulation of multiple targets in the brain may lead to an improved response to treatment. In particular, the inventors have found that response to neurostimulation of the various targets in the brain may be improved by additional neurostimulation of the lateral habenula (LH) and the posterior commissure (PC).

Thus, at its most general, the invention provides a method of treatment performed on a subject's brain, which involves applying one or more neuromodulation signals to the LH and the PC.

According to a first aspect of the invention, there is provided a method of treatment performed on a subject's brain, the method including a step of applying one or more neuromodulation signals to the lateral habenula (LH) and the posterior commissure (PC).

The LH and PC may be stimulated via the same (single) neuromodulation signal. Alternatively, separate (different) neuromodulation signals may be applied to each of the LH and PC respectively.

Stimulation of the LH and PC may affect the adjacent medial thalamus, and/or periventricular gray, and/or periaqueductal gray and/or their respective projections; and may, via the LH and PC, influence the pineal gland and/or the contralateral hemispheric projections. Therefore, applying one or more neuromodulation signals to the LH and PC may include directly or indirectly applying one or more neuromodulation signals to one or more of the adjacent medial thalamus, periventricular gray, periaqueductal gray and their respective projections; and may include, via the LH and PC, influencing one or both of the pineal gland and the contralateral hemispheric projections.

A neuromodulation signal may be an electrical signal applied to a target in the brain. For example, a neuromodulation signal may be a pulsed electrical signal. Parameters of the neuromodulation signal, such as frequency, pulse width and pulse amplitude may be adjusted depending on particular requirements of the treatment. The neuromodulation signals may be applied continuously, or in bursts or cycles.

The inventors have found that neurostimulation of the LH and PC in a subject may enhance cerebral blood flow. This may enable a wide variety of conditions which are linked with reductions in cerebral blood flow to be treated.

The lateral habenula is part of the habenula complex which includes medial and lateral nuclei. By way of the stria medullaris, the medial habenula nucleus receives fibres from the medial septal-diagonal band complex. The medial habenula nucleus is also in receipt of fibres from the periaqueductal gray matter, serotonergic projection from the mesencephalic raphe nucleus and adrenergic innervation from the superior cervical ganglion. The efferents of the medial habenula nucleus terminate exclusively in the interpeduncular nucleus, which project massively to the dorsal raphe and central superior nuclei. The lateral habenula nucleus receives its afferents principally from the nuclei of the diagonal band, lateral pre-optico-hypothalamic area, substantia innominata and the medial pallidal segment; whereas the ventral tegmental area, and mesencephalic raphe nuclei and ventral part of the periaqueductal gray matter give rise to ascending input to this nucleus. Efferent fibres from the lateral habenula nucleus descend in the fasciculus retroreflexus and terminate in the various mesencephalic centres including the pars compacta of the substantia nigra, ventral part of the periaqueductal gray, dorsal raphe and central superior nuclei and mesencephalic reticular formation. Whilst the functional role of habenula nuclei is not fully elucidated, their fibre connections suggest that they represent processing stations for a variety of biological functions, including pain processing, emotion, reproduction, nutrition, stress responses, sleep waking cycles and learning.

The posterior commissure is a rounded band of white fibres crossing a middle line on the dorsal aspect of the rostral end of the cerebral aqueduct. Most of the fibres originate in the nucleus of the posterior commissure which lies in the periaqueductal gray of the rostral end of the cerebral aqueduct, in front of the oculomotor nucleus; and other fibres are thought to be derived from the posterior part of the thalamus, the superior colliculus and the medial longitudinal fasciculus. On the basis of clinical observations, the nucleus of the posterior commissure has been suspected as being involved in the generation of upward eye movements and pre-motor control of the upper eyelid. The nucleus projects to contralateral thalamic, internal capsule and midbrain locations. The nucleus has reciprocal connections with the adjacent central mesencephalic reticular formation which receives input from the cerebellar fastigial nucleus, which when stimulated has been shown to procure neuroprotection in stroke.

The ventral PC is closely related to the subhabenular nucleus, fasciculus retroflexus (habelular projection to the midbrain) and medial thalamic parafascicular nucleus. Therefore, applying a neuromodulation signal to the PC may include also applying directly or indirectly a neuromodulation signal to one or more of the subhabenular nucleus, fasciculus retroflexus (habelular projection to the midbrain) and medial thalamic parafascicular nucleus.

The method may further include applying one or more neuromodulation signals to one or more additional targets in the subject's brain. Thus, one or more neuromodulation signals may be applied to the LH and PC in combination with one or more additional targets in the subject's brain. The inventors have found that combining neurostimulation of a brain target with neurostimulation of the LH and PC may result in an improved response to neurostimulation of the target.

The same (single) neuromodulation signal may be applied to each of the LH and PC and the one or more additional targets in the subject's brain. Alternatively, different neuromodulation signals may be applied to each of, or subsets (groups) of, the LH and PC and the one or more additional targets in the subject's brain.

The one or more additional targets may include the dorsomedial nucleus of the thalamus (DMN).

Therefore, according to one embodiment, the method includes applying one or more neuromodulation signals to each of the DMN, the LH and the PC.

The inventors have found that a subject's response to neurostimulation of the DMN may be improved by combining neurostimulation of the DMN with neurostimulation of the LH and the PC. Accordingly, the method of the first aspect may improve a subject's response to neurostimulation of the DMN, which may result in an improved outcome of treatments involving neurostimulation of the DMN.

The DMN has extensive and reciprocal connections with the prefrontal cortex and limbic structures including the limbic cortex, hippocampus and basolateral amygdala. The DMN participates in higher cognitive functions, such as spatial working memory, and emotional processes. The DMN is also involved in processing pain. In schizophrenia, there is reduced volume and neuronal number in the DMN. The DMN also plays the main role in amygdala hippocampal seizures and controls limbic seizures. The DMN is closely related to the centromedian parafascicular nucleus complex. The DMN and the centromedian parafascicular complex are embedded in different basal ganglia—thalamo-cortical loops, which integrate cognitive and emotional aspects of human behaviour. The parvocellular sector of the DMN is involved in memory recall. The magnocellular sector in monkeys is required for new learning; and specific damage in humans is associated with both retrograde and anterograde amnesia. Acute isolated disorientation of time can occur with small artery disease of the thalamus involving the DMN.

Neurostimulation may, for example, be used to alter emotional response and memory. For example, high frequency neurostimulation of the DMN may serve to improve memory formation. Accordingly, neurostimulation of the DMN may enable treatment of a range of conditions (see Mavridis I, Human Mediodorsal Thalamic Nucleus as a Potential Target for Deep Brain Stimulation; Review of the Literature and Anatomical Considerations. O A Anatomy 2014 Jan. 12; 2(1)-1.).

The one or more additional targets may include the posterior nucleus of the hypothalamus. Therefore, according to one embodiment, the method includes applying one or more neuromodulation signals to each of the posterior nucleus of the hypothalamus, the LH and the PC (and optionally the DMN). The inventors have found that stimulation of the posterior nucleus of the hypothalamus may result in an increase cerebral blood flow and cerebral blood volume, as well as reduce mean transit time of blood through the brain. Stimulation of the posterior nucleus of the hypothalamus may be used to treat cluster headaches.

The one or more neuromodulation signals may include multiple neuromodulation signals. For example, the one or more neuromodulation signals may include a first neuromodulation signal that is applied to the DMN, a second neuromodulation signal that is applied to the LH, and a third neuromodulation signal that is applied to the PC. In other cases, a same neuromodulation signal may be applied to multiple targets. For example, a first neuromodulation signal may be applied to the DMN, whilst a second neuromodulation signal may be applied to the LH and the PC.

Neuromodulation signals may be applied to the LH and the PC, and any additional targets in the brain, via an electrode lead that is implanted into the subject's brain. The electrode lead may have a plurality electrodes which are arranged to apply neuromodulation signals to each of the LH and the PC and any additional targets (e.g. the DMN). For example, the electrode lead may include a first electrode arranged to apply a neuromodulation signal to the DMN, a second electrode arranged to apply a neuromodulation signal to the LH, and a third electrode arranged to apply a neuromodulation signal to the PC. The same or different neuromodulation signals may be applied to each of the LH and the PC and any additional targets in the brain. The electrode lead may be arranged so that separate neuromodulation signals may be applied via each of the electrodes. In this manner, the different targets may be individually stimulated. In some cases, multiple targets may be stimulated via the same electrode.

The different targets (e.g. LH, PC, DMN) may be stimulated simultaneously or sequentially.

In some embodiments, a first neuromodulation signal having a first frequency may be applied to the dorsomedial nucleus, and one or more second neuromodulation signals may be applied to the lateral habenula and the posterior commissure, wherein each of the one or more second neuromodulation signals has a frequency lower than the first frequency.

The higher frequency neuromodulation signal applied to the DMN may serve to inhibit neurons in the DMN, whilst the lower frequency neuromodulation signals applied to the LH and the PC may serve to enhance the subject's response to the treatment. The first and second neuromodulation signals may be applied via different sets of electrodes on the electrode lead. The first neuromodulation signal may correspond to a first pulse train having the first frequency, whilst the second neuromodulation signals may correspond to a second pulse train having the second frequency.

The same second neuromodulation signal may be applied to both the LH and PC.

Alternatively, different second neuromodulation signals having, for example, different frequencies, may be applied to each of the LH and PC respectively.

The first neuromodulation signal applied to the DMN may have a frequency within a higher end of the gamma range (30 to 100 Hz), or higher.

The second neuromodulation signal applied to the LH may be in theta (4 to 8 Hz), alpha (8 to 14 Hz) and beta (14 to 30 Hz) frequency ranges. Stimulation of the LH may also incorporate the habenula commissure, and pineal commissure with transmission of stimulation to the pineal gland. Stimulation of the LH may be varied to calibrate and synchronise with circadian rhythm.

The second neuromodulation signal applied to the PC may be within theta (4 to 8 Hz) and alpha (8 to 14 Hz) frequency ranges; and potentially up to 30 to 40 Hz.

In one example, the first frequency may be greater than 70 Hz, and each of the one or more second neuromodulation signals may have a frequency between 4 and 50 Hz. In some examples, the same neuromodulation signal may be applied to the LH and PC, whilst in other examples, separate/different neuromodulation signals may be applied to the LH and PC.

The stimulation applied at different frequencies may be interlacing and whilst it can be applied continuously, fluctuations may be programmed delivering stimulation with burst frequencies or programmed with appropriate on/off periods; and established from algorithms deciphered from mathematical decoding of normal and disease state local field potentials and brain rhythm coherences as seen over the circadian rhythm.

In some embodiments, the one or more additional targets may include the ventrolateral periaqueductal gray (VL-PAG). Thus, according to an embodiment the method includes applying one or more neuromodulation signals to each of the LH, PC and VL-PAG (and optionally the DMN).

In this manner, combined neurostimulation of the DMN, VL-PAG, LH and PC may be performed. In US 2016/0367809 A1, the inventors disclosed that combined neurostimulation of the DMN and the VL-PAG may serve to increase perfusion of the hippocampus and other structures involved in cognition and memory. As a result, combined neurostimulation of the DMN and the VL-PAG may enable treatment of various conditions, including Alzheimer's disease, hypertension and epilepsy. The inventors have further found that additionally applying neurostimulation signals to the LH and the PC may improve a subject's response to combined neurostimulation of the DMN and the VL-PAG.

The neuromodulation signal applied to the VL-PAG may be one of the one or more second neuromodulation signals discussed above. In this manner, the first, higher frequency, neuromodulation signal may be applied to the DMN, whilst lower frequency neuromodulation signal(s) may be applied to the LH, PC and VL-PAG. The neuromodulation signal applied to the VL-PAG may be the same as the neuromodulation signal applied to the LH and/or the PC, or may be different to the neuromodulation signal applied to the LH and/or the PC.

The neuromodulation signal applied to the VL-PAG may be within theta (4 to 8 Hz) and alpha (8 to 14 Hz) frequency ranges; and potentially up to 30 to 40 Hz.

In one example, the neuromodulation signal applied to the VL-PAG may have a frequency between 5 and 50 Hz. Low frequency (e.g. 5 to 50 Hz) stimulation of the VL-PAG may result in a global increase in cerebral blood flow and cerebral blood volume, and a reduction in blood mean transit time.

The periventricular gray (PVG) and periaqueductal gray (PAG) have been recognised as targets for the brain stimulation in the treatment of intractable pain since 1977. The PAG resides within the mid brain and its role in autonomic function has been studied extensively in animal models discovering that it is critically involved in mediating the defence response to perceived or present dangers. Perceived escapable fear elicits a fight-or-flight response; and in contrast perceived inescapable fear, where it is advantageous to remain undetected, causes the opposite response pattern of freezing. Both responses are mediated from the PAG but from separate sites; the dorsal PAG produces the fight and flight response whereas the ventral portion (VL-PAG) produces the freezing response.

The freezing response consists of hypotension, bradycardia and hyperventilation and is often coupled with analgesia, and is mediated by the VL-PAG, which also has dense projections to known cardiovascular integration sites within the central nervous system (CNS) including medullary and hypothalamic nuclei in addition to those involved in motor control and analgesia. The VL-PAG also receives projections from regions involved in somatosensory feedback and autonomic regulation including forebrain cortical structures, the limbic system, spinal afferents and hypothalamic nuclei.

In some embodiments, the method may further include: identifying a trajectory in the subject's brain, the trajectory linking the dorsomedial nucleus and the VL-PAG across the lateral habenula and the posterior commissure; and implanting an electrode lead into the subject's brain along the identified trajectory, the electrode lead including a plurality of electrodes for applying the one or more neuromodulation signals. In this manner, the neuromodulation signals described above may be applied using a single electrode lead which spans a trajectory linking the DMN, LH, PC and VL-PAG. This may facilitate neurostimulation of the DMN, LH, PC and VL-PAG, and avoid having to use multiple electrode leads to stimulate these different targets. Additionally, having an electrode lead which spans such a trajectory may enable different combinations of neuromodulation signals to be applied to one or more of the DMN, LH, PC and VL-PAG. This may enable a neurostimulation treatment to be tailored according to the subject's needs. The trajectory may be transventricular, i.e. it may pass via the lateral ventricle.

The wording "across the lateral habenula and the posterior commissure" may mean that the trajectory passes from one side of the lateral habenula and the posterior commissure to another side of the lateral habenula and the posterior commissure. Typically the trajectory will be spaced from the lateral habenula and the posterior commissure and will pass adjacent to the lateral habenula and the posterior commissure.

The trajectory may be identified prior to implantation of the electrode lead, for example by obtaining images (e.g. via computed tomography and/or magnetic resonance imaging) of the subject's brain and plotting the trajectory in the subject's brain. The electrode lead may be implanted into the subject's brain along the identified trajectory, for example using a stereotactic frame and/or stereotactic robot.

After implantation, the electrode lead may follow a substantially straight line trajectory which passes through the lateral ventricle, into the DMN bypassing the third ventricle, adjacent to the LH and the PC, and into the VL-PAG. Preferably, the trajectory of the electrode lead passes adjacent to the LH and the PC, without contacting the LH or PC, in order to avoid damage to the LH and PC.

The trajectory may further encompass the anterior nucleus of the thalamus, so that a neuromodulation signal may be applied to the anterior nucleus of the thalamus. Neurostimulation of the anterior nucleus of the thalamus may enable treatment of epilepsy.

The trajectory may also further encompass the centromedian and/or parafascicular nuclei of the thalamus, so that neuromodulation signals may be applied to these parts of the thalamus.

The plurality of electrodes on the electrode lead may be arranged so that, after implantation of the electrode lead, a neuromodulation signal may be applied to each of the DMN, LH, PC and VL-PAG via electrodes in the plurality of electrodes. In some cases, each of the DMN, LH, PC and VL-PAG may be stimulated via a respective electrode in the plurality of electrodes. The electrodes on the electrode lead may be isolated from one another, so that each target may be individually stimulated.

The plurality of electrodes on the electrode lead may be regularly (evenly) spaced along a portion of the electrode lead which spans from the DMN to the VL-PAG. This may enable neuromodulation signals to be applied to targets along the entire length of the trajectory between the DMN and the VL-PAG. For example, the plurality of electrodes may span a length of between 20-30 mm on the electrode lead, e.g. on a distal portion of the electrode lead. In one example, the plurality of electrodes may include eight electrodes having a length of about 1.5 mm each, with 1.5 mm intervals between adjacent electrodes. In another example, the plurality of electrodes may include twelve electrodes having a length of about 1.5 mm each, with 0.5 mm intervals between adjacent electrodes.

The electrode lead may be implanted unilaterally into a hemisphere of the brain, preferably into the non-dominant hemisphere of the brain. The non-dominant hemisphere is normally the right side, contralateral to the side that primarily controls speech processing. Implanting the electrode lead unilaterally into one hemisphere may minimise surgical time and the risk of complications such as haemorrhage. However, in some cases, clinical outcome may be improved by applying the neuromodulation signals to targets in both hemispheres. In such a case, electrode leads may be implanted into both hemispheres.

The right and pre-dominantly non-dominant hemisphere has been shown to have greater lateralization for cognitive and emotional processing, and behavioural expression, and may be preferable to target and enable procurement of a more optimal response. Therefore, the electrode lead may be implanted unilaterally into the right hemisphere of the brain.

Implanting the electrode lead may involve first implanting a guide tube into the user's brain, through which the electrode lead is then inserted.

The trajectory may be arranged such that a spacing between the electrode lead and the lateral habenula is less than 5 mm, and/or a spacing between the electrode lead and the posterior commissure is less than 5 mm. A spacing of 5 mm or less between the electrode lead and the LH and PC may ensure that the LH and PC can be reliably stimulated via electrodes on the electrode lead. In particular, an electrode which is used to apply a neuromodulation signal to the LH may be less than 5 mm from the LH, and an electrode which is used to apply a neuromodulation signal to the PC may be less than 5 mm from the PC. The inventors have found that a spacing greater than 5 mm may prevent effective stimulation of the LH and PC, which may reduce the overall effectiveness of the treatment. For example, the spacing between the electrode lead and the LH may preferably be 4 mm, 3 mm, 2 mm, or 1 mm, or less than any of these values. Similarly, the spacing between the electrode lead and the PC may preferably be 4 mm, 3 mm, 2 mm, or 1 mm, or less than any of these values. Preferably, a spacing between the electrode lead and the lateral habenula is less than 2 mm, and/or a spacing between the electrode lead and the posterior commissure is less than 2 mm.

In some embodiments, the method may further include applying a neuromodulation signal to the dorsal anterior cingulate cortex (DACC) and/or the corpus callosum (CC). The inventors have found that in some cases, response to treatment may be improved by additional neurostimulation of the DACC and/or the CC. Thus, neurostimulation of one or more of the DMN, LH, PC and VL-PAG may be enhanced by combined neurostimulation of the DACC and/or CC. The DACC and the CC may be stimulated via the same or different electrodes.

The inventors have found that stimulation of the DACC and/or CC in combination with the LH and PC may further improve a patient's response to neurostimulation.

In one test subject, the inventors have found that bilateral stimulation of the DACC in combination with the LH, PC and VL-PAG results in a positive response of the subject to the neurostimulation. Additionally applying a neuromodulation signal to the DMN may provide further stimulation of limbic circuitry. Applying a neuromodulation signal to the CC (e.g. unilaterally) may enable further commissural spread which may bilaterally enhance cerebral blood flow.

The neuromodulation signal applied to the DACC and/or CC may have a frequency within the gamma band (e.g. 30 to 100 Hz).

The neuromodulation signal applied to the DACC and/or CC may have a high frequency, e.g. a frequency greater than 70 Hz.

In one approach, a single electrode lead may be used to apply the neuromodulation signals to one or more of the DACC, CC, DMN, LH, PC and VL-PAG. In such an approach, the trajectory may further pass adjacent the dorsal anterior cingulate cortex and the electrode lead may include an electrode arranged to apply the neuromodulation signal to the dorsal anterior cingulate cortex; and/or the trajectory may further pass adjacent the corpus callosum and the electrode lead may include an electrode arranged to apply the neuromodulation signal to the corpus callosum. Where both the DACC and the CC are stimulated, the trajectory may pass adjacent to both the DACC and the CC, and the same electrode may be used to apply a neuromodulation signal to both the DACC and the CC. In some cases, separate electrodes may be used to stimulate the DACC and the CC. Using a single electrode lead to stimulate the multiple targets may minimise surgical time, and reduce a number of implants required for a subject. Preferably, the trajectory may pass 5 mm or less from the DACC and/or CC, to ensure that the DACC and CC may be effectively stimulated via the electrode lead.

In another approach, a separate electrode lead may be used to stimulate the DACC and/or CC. Thus, the method may further include implanting a second electrode lead into the subject's brain, the second electrode lead including an electrode arranged to apply the neuromodulation signal to the dorsal anterior cingulate cortex.

A separate electrode lead targeting the DACC and/or CC may be used when it is felt that a transventricular trajectory that links up the DMN, LH, PC and VL-PAG cannot safely incorporate the DACC and/or CC without impacting on intraventricular vascular structures or the sagittal sinus.

In one example, the separate electrode lead may have a single electrode (e.g. cylindrical electrode) on the electrode lead that extends across the DACC and into the CC. Alternatively, a separate electrode lead having multiple electrodes arranged to stimulate the DACC and CC separately may be used.

In some embodiments, the method may further include detecting a physiological parameter of the subject, and adjusting at least one of the one or more neuromodulation signals based on the detected physiological parameter. In this manner, the physiological parameter may be used as feedback for adjusting the neuromodulation signals. This may enable more accurate and effective neurostimulation of the brain, as the neuromodulation signals may be adjusted based on the subject's response to the signals.

For example, the physiological parameter may include one or more of the subject's blood pressure, blood flow, cerebral blood flow, and intracranial pressure.

The physiological parameter may be monitored via one or more sensors that are placed on, or implanted into the subject's body.

Where neuromodulation signals are applied to the VL-PAG, the DACC and/or CC, the neuromodulation signals applied to the VL-PAG, the DACC and/or CC may be adjusted based on the detected physiological parameter.

Where the one or more neuromodulation signals are applied in bursts, the neuromodulation signals may be based on measurements of the physiological parameters obtained between bursts of the one or more neuromodulation signals.

Adjusting a neuromodulation signal may involve adjusting one or more parameters of the neuromodulation signal, such as frequency, pulse width and pulse amplitude. In some cases, a set point may be associated with the physiological parameter, and the neuromodulation signal may be adjusted until the set point is reached.

Where more than more neuromodulation signal is applied, one, more than one, or all of the neuromodulation signals may be adjusted based on the detected physiological parameter.

In some embodiments, the method may further include adjusting at least one of the one or more neuromodulation signals based on the subject's circadian rhythm.

For example, one or more parameters (e.g. frequency, pulse width and pulse amplitude) of the one or more neuromodulation signals may be adjusted or modulated depending on a time in the subject's circadian rhythm.

In particular, the one or more neuromodulation signals may be modulated to reflect a circadian rhythm with reduced nocturnal activity. This may serve to ensure that the subject's circadian rhythm is not disrupted by the application of the neuromodulation signals. This may also serve to maintain and/or re-establish the subject's circadian rhythm.

Where neuromodulation signals are applied to the VL-PAG, the DACC and/or CC, the neuromodulation signals applied to the VL-PAG, the DACC and/or CC may be modulated based on the subject's circadian rhythm.

In order to re-establish the subject's circadian rhythm, a stimulation prescription (i.e. stimulation schedule) for the one or more neuromodulation signals may be adjusted to reflect the circadian rhythm and coincide with fluctuating tonic firing, e.g. as typically seen within the circuits and circadian neurons.

For example, in one embodiment the method may include applying a low frequency stimulation (e.g. 5 to 50 Hz) to the LH and PC during the day, and then applying both a low frequency stimulation (e.g. 5 to 50 Hz) to the LH and PC and a high frequency stimulation (e.g. a frequency greater than 70 Hz) to the DMN during the night. Alternatively, applying both a low frequency stimulation (e.g. 5 to 50 Hz) to the LH and PC and a high frequency stimulation (e.g. a frequency greater than 70 Hz) to the DMN during the day and night, but with reduced amplitude of the current of the high frequency stimulation to the DMN during the day, and conversely increased amplitude of current of the high frequency stimulation to the DMN at night. Alternatively, applying both a low frequency stimulation (e.g. 5 to 50 Hz) to the LH and PC and a high frequency stimulation to the DMN during the day and night, but with reduced amplitude of the high frequency stimulation (e.g. 50 to 70 Hz) to the DMN during the day, and conversely increased amplitude the high frequency (e.g. greater than 70 Hz) stimulation to the DMN at night. Alternatively, during the night, a high frequency stimulation signal may be applied to the DMN and LH, and a low frequency stimulation signal may be applied to the PC.

Adjusting the one or more neuromodulation signals based on the subject's circadian rhythm may involve monitoring a physiological parameter of the subject (e.g. blood pressure, heart rate, heart rate variability, pulse wave variability, muscle sympathetic nerve activity, body positional change, brain EEG, brain slow wave activity), to determine the subject's circadian rhythm. The one or more neuromodulation signals may then be adjusted based on the determined circadian rhythm. Indeed, a subject's blood pressure and heart rate may vary with circadian rhythm such that blood pressure and heart rate are higher during the day and lower at night. In this manner, diurnal variations in blood pressure and/or heart rate may be monitored to determine a subject's circadian rhythm.

In some cases, the method may involve detecting a disturbance in the subject's circadian rhythm, e.g. by recording diurnal variations of a physiological parameter of the subject (e.g. blood pressure and/or heart rate) and comparing the recorded diurnal variations to model variations corresponding to a non-disturbed circadian rhythm.

The method may further involve adjusting at least one of the one or more neuromodulation signals to attempt to correct a detected disturbance in a subject's circadian rhythm.

A disturbance in a subject's circadian rhythm may be detected based on a correlation of a disturbed sleep/wake cycle of the subject and recorded local field potentials in one or more targets in the subject's brain (e.g. one or more of the LH, PC, DMN, VL-PAG, DACC, CC).

The circadian rhythm of blood pressure is associated with a high span during the awake period and a low span during the sleep period. Cardiovascular events may occur more frequently in the early morning period, the time when blood pressure and heart rate rise steeply. Patients who have an excess of morning surge in blood pressure and those who lack the normal nocturnal blood pressure fall (so-called "non-dippers") have been shown to have an excessive incidence of strokes, heart failure and other cardiovascular events. While there are numerous physiologic mechanisms underlying abnormalities in the 24-hour blood pressure profile, including abnormalities and sympathetic nervous system activity, salt and volume balance, and activation of the Renin Angiotensin-Aldosterone System, for many patients the mechanisms remain unclear. The normal circadian rhythm of blood pressure has a nocturnal decrease of 15-25% in blood pressure compared to awake values. However in 25-40% of patients with hypertension, a non-dipper pattern is present. Clinical studies in patients with hypertension have found that a blunted nocturnal BP decrease occurs when there is an increase in adrenergic activity and a decrease in vagal activity during sleep.

Parameters of the one or more neuromodulation signals may, for example, be determined by recording local field potentials across one or more targets in the brain (e.g. one or more of the DMN, LH, PC, VL-PAG, DACC, CC). An analysis of the recorded field potentials may then be performed to determine appropriate stimulation parameters, e.g. in order to enhance cerebral perfusion and/or re-establish a normal circadian rhythm. The neuromodulation signals may also be adjusted based on sensing of a disturbed rhythm (e.g. the circadian rhythm).

The local field potentials may be recorded using electrodes on the electrode lead that is implanted in the subject's brain.

Local field potentials across one or more targets in the brain may be recorded in normal and diseased states using animal models to generate computational and mathematical models. Local field potentials recorded in human disease states may be used to further refine aetiological and individualistic stimulation parameters, e.g. in anticipation of re-establishing a normal circadian rhythm and rebalance autonomic imbalance.

The method may further include applying a stimulation signal to a carotid body and/or a carotid baroreceptor in the subject. Such a method may be considered as an independent aspect of the invention. More generally, in such an independent aspect, one or more neuromodulation signals may be applied to one or more targets in the subject's brain, without necessarily being limited to the targets discussed above. Thus, an independent aspect of the invention may provide a method of treatment performed on a subject, the method including: applying one or more neuromodulation signals to one or more targets in the subject's brain; and applying a stimulation signal to a carotid body and/or a carotid baroreceptor in the subject.

The inventors have found that combining neurostimulation of targets in the subject's brain with stimulation of a carotid body and/or a carotid baroreceptor in the subject may result in an enhanced cerebral blood flow, and enable a more accurate control of cerebral blood flow. Indeed, as the carotid body and carotid baroreceptors are involved in regulation of blood flow and blood pressure, combined stimulation of a target in the subject's brain and the carotid body and/or a carotid baroreceptor may have a synergistic effect in terms of enhancing and controlling brain perfusion. The one or more targets in the subject's brain to which a neuromodulation signal is applied may be selected in order to cause an increase in brain perfusion.

Stimulation of the carotid body and/or carotid baroreceptor may be performed simultaneously with neurostimulation of targets in the brain. This may augment response through both retrograde peripheral reflex signalling from the carotid body to the brain and anterograde from the brain stimulation to the periphery. As a result cerebral blood flow may be enhanced.

The one or more neuromodulation signals may be applied via an electrode lead implanted into the subject's brain, for example as described above. Thus, neuromodulation signals may be applied to the LH and PC, optionally the VL-PAG and/or DMN, and optionally the DACC and/or CC. As discussed above, stimulation of these targets may lead to an improved brain perfusion, enabling treatment of a wide variety of conditions.

In one embodiment, stimulation of a carotid body and/or a carotid baroreceptor may be combined with simultaneous neurostimulation of the LH, PC, DMN and VL-PAG.

The stimulation signal may be applied to a carotid body and/or a carotid baroreceptor via one or more stimulation electrodes implanted into the subject and/or placed in contact with the subject. The stimulation signal may be applied to a carotid body and/or a carotid baroreceptor according to a method described in the inventors' earlier application, US 2015/0112359 A1, which is incorporated herein by reference. For example, the stimulation signal may be a pulsed radiofrequency (RF) electrical signal applied to the carotid body and/or carotid baroreceptor via an electrode implanted into the subject.

Electrical stimulation (e.g. with a pulsed RF signal) may modify the function of a carotid body or bodies such that nerve signals from those bodies may be attenuated or eliminated. An effect of this may be that average arterial blood pressure is reduced for a period of days, weeks or months following treatment.

Carotid baroreceptors are nerve endings located in the wall of the aortic arch and the carotid sinus that detect changes in arterial pressure through stretch of the vessel walls. The baroreceptors are stimulated by stretching and their firing rate increases with pressure. Below a mean pressure of about 60 mmHg, action potential frequency reaches a minimum; above about 160 mmHg the baroreceptors reach a maximum firing rate such that further increases in pressure do not produce an increase in firing rate. Denervation of the baroreceptors in humans produces a long term increase in mean arterial pressure and increased heart rate. Conversely, stimulation of the baroreceptors using an electrical pulse generator may provide a reduction in blood pressure over the long term.

Carotid baroreceptors may be located in the carotid sinus and the aortic arch. So, for example, a carotid baroreceptor may be stimulated via a stimulation electrode implanted in close proximity to the carotid sinus and/or the aortic arch. A carotid body may be stimulated via an electrode implanted at or near the carotid body. In some cases, multiple stimulation electrodes may be used, to enable stimulation of multiple targets.

The method of the invention may be for treating one or more of hypertension, a traumatic brain injury, cerebral vasospasm, cerebral infarction, a brain tumour, cerebral glioma, Parkinson's disease, Alzheimer's disease, vascular dementia, fronto-temporal dementia, other dementias, amyotrophic lateral sclerosis, motor neurone disease, Huntington's disease, multiple system atrophy, multiple sclerosis, addiction, depression, post-traumatic stress disorder, schizophrenia, obesity, renal failure, epilepsy and attention deficit hyperactivity disorder. However, the method of the present invention may also or alternatively be used for treating other conditions, and especially those associated with reduction in cerebral blood flow.

Neurostimulation for different conditions may be based on established computational mathematical modelling based on local field potential recording along targets in the brain. Detection of one or more physiological parameters (as discussed above) may be combined with simultaneous adjustment of the one or more neuromodulation signals in between bursts of the one or more neuromodulation signals.

The one or more neuromodulation signals may be adjusted based on one or more of transcranial brain activity, cerebral blood flow, and sympathetic nerve monitoring, e.g. to optimise the one or more neuromodulation signals in anticipation of re-establishing cerebral blood flow, circadian rhythm, and correcting autonomic imbalance.

The above conditions may be linked with one or more of a reduction in cerebral blood flow, autonomic imbalance, a disruption in the circadian rhythm, altered brain coherence, cortical spreading depolarizations and brain rhythm desynchronisation. The inventors have found that neurostimulation of the LH and PC, optionally in combination with the DMN and/or the VL-PAG, and optionally the DACC and/or CC may enhance cerebral blood flow, which may restore autonomic imbalance and re-establish circadian rhythm. As a result, the method of the invention may be used to treat one or more of the above conditions. The specific combination of neuromodulation signals used may be tailored to the subject and condition treated.

According to a second aspect of the invention, there is provided an apparatus for performing a treatment on a subject's brain, the apparatus comprising: an electrode lead arranged for insertion into the subject's brain, a distal portion of the electrode lead having a plurality of electrodes arranged to apply one or more neuromodulation signals to the lateral habenula and the posterior commissure; and a controller configured to generate the one or more neuromodulation signals applied by the plurality of electrodes.

The apparatus may be used to perform a method according to the first aspect of the invention. Accordingly, features of the first aspect of the invention may be shared with the second aspect of the invention.

The electrode lead may be inserted into the subject's brain in order to apply neuromodulation signals to targets in the subject's brain via the plurality of electrodes on the distal portion of the electrode lead.

The plurality of electrodes may be dimensioned and arranged on the electrode lead so that each of the LH and PC may be stimulated via the plurality of electrodes.

For example, the positioning, and/or individual length, and/or spacing and/or total length of the plurality of electrodes may be configured so that each of the LH and PC may be stimulated via the plurality of electrodes, for example so that an electrode of the plurality of electrodes can be positioned proximal to each of the DMN, LH and PC.

The plurality of electrodes may be further arranged to apply one or more neuromodulation signals to one or more additional targets in the subject's brain. In this manner, neurostimulation of the LH and PC may be combined with neurostimulation of additional targets in the brain.

The one or more additional targets may include the dorsomedial nucleus of the thalamus. In other words, the plurality of electrodes may be arranged to apply one or more neuromodulation signals to each of the DMN, LH and PC.

The plurality of electrodes may include two or more electrodes. For example, the plurality of electrodes may include a first electrode for stimulating the DMN, a second electrode for stimulating the LH and a third electrode for stimulating the PC. In some cases, a single electrode may be used to stimulate both the LH and the PC, e.g. where the electrode has a sufficient length to apply a neuromodulation signal to both targets. The electrodes in the plurality of electrodes may be electrically isolated from one another, so that the different targets may be individually stimulated.

The one or more additional targets may include the VL-PAG. Thus, the plurality of electrodes may be further arranged to apply a neuromodulation signal to the VL-PAG.

In this manner, neuromodulation signals may be applied to each of the LH and PC and optionally the VL-PAG and/or DMN. For example, the plurality of electrodes may include an electrode arranged (e.g. positioned and dimensioned) to apply a neuromodulation signal to the VL-PAG.

The electrode lead may be dimensioned for insertion into the user's brain. For example, an outer diameter of the electrode lead may be around 1.3 mm or less. The electrode lead may be configured for implantation along a straight line trajectory linking the DMN and the VL-PAG across the LH and the PC, as described in relation to the first aspect of the invention.

The electrode lead may be in the form of an elongate cable having a generally cylindrical shape. The cable may include a set of wires extending through and connected to the plurality of electrodes, so that electrical signals (e.g. neuromodulation signals) may be conveyed to the electrodes.

Each of the wires may be electrically coupled to the controller at a proximal end of the electrode lead, so that neuromodulation signals generated by the controller may be conveyed to the electrodes via the wires.

The electrode lead may include an outer protective sheath arranged to electrically insulate the electrode lead and protect it from the environment.

The plurality of electrodes may be exposed on a surface of the electrode lead, so that they may come into contact with brain tissue to apply a neuromodulation signal thereto.

An electrode in the plurality of electrodes may have a ring or cylindrical shape, i.e. it may extend around a circumference of the electrode lead. In this manner, the electrode may apply the neuromodulation signal substantially uniformly about a longitudinal axis of the electrode lead.

Alternatively, an electrode in the plurality of electrodes may be configured to apply a neuromodulation signal in a particular direction, e.g. the electrode may extend around only a portion of the circumference of the electrode lead.

The electrodes in the plurality of electrodes may all be identical, or they may have different shapes, sizes and directions (e.g. depending on the specific target they are intended to stimulate).

In one embodiment, a combination of directional (e.g. extending around only a portion of the circumference of the electrode lead) and non-direction (e.g. a cylindrical electrode) electrodes may be provided.

In other embodiments, all of the electrodes may be non-directional (e.g. cylindrical electrodes) or all of the electrodes may be directional (e.g. extending around only a portion of the circumference of the electrode lead).

The controller is configured to generate the one or more neuromodulation signals applied by the plurality of electrodes. Accordingly, the controller may include appropriate electronic circuitry for generating the one or more neuromodulation signals. As noted above, the plurality of electrodes may be connected to the controller via a set of wires in the electrode lead, which are arranged to convey the neuromodulation signals to the electrodes.

The controller may be configured to apply different neuromodulation signals via different electrodes in the plurality of electrodes.

For example, the controller may be configured to apply a first neuromodulation signal having a first, higher frequency (e.g. greater than 70 Hz) to the DMN via a first electrode, and to apply a second neuromodulation signal having a second, lower frequency (e.g. between 5 and 50 Hz) to the LH and PC via second and third electrodes.

The controller may be configured to apply neuromodulation signals in accordance with a method of the first aspect of the invention.

In some cases, two or more of the plurality of electrodes may be arranged in pairs, e.g. so that a first electrode in a pair may act as an anode, and a second electrode in the pair may act as a cathode. This may enable bipolar stimulation of brain tissue located between a pair of electrodes.

In some cases, one or more of the plurality of electrodes may be arranged for monopolar stimulation. For example, an electrode on the electrode lead may act as a cathode, with a guide tube or a case of the controller acting as an anode.

The controller may be in the form of an implantable pulse generator (IPG). The IPG may be arranged for implantation in the subject's skull, e.g. in a pocket formed in the subject's skull.

In some embodiments, the plurality of electrodes may be evenly spaced in a longitudinal direction along a length of the distal portion of the electrode lead. In other words, the plurality of electrodes may include a linear array of evenly spaced electrodes arranged along the length of the distal portion of the electrode lead. This may enable targets to be stimulated along substantially the entire length of the distal portion of the electrode lead. Distances between targets in the brain (e.g. the DMN, LH, PC, VL-PAG) may vary from subject to subject. Such variations may be accommodated for by using a linear array of evenly spaced electrodes, as different electrodes in the linear array may be used to stimulate the targets, depending on the specific locations of the targets in the subject's brain.

The number of evenly spaced electrodes and their spacing may be selected based on the targets to be stimulated, and on a desired spatial resolution for application of the neuromodulation signals. For example, a large number of closely spaced electrodes may enable more accurate stimulation of a target, by selecting an electrode closest to the target.

The plurality of evenly spaced electrodes may span a length between 20-25 mm. In this manner, the plurality of electrodes may span a distance between the DMN and the VL-PAG. This may enable targets lying on a trajectory between the DMN and the VL-PAG to be stimulated with the electrodes. In particular, it may enable treatment of the LH and PC when the electrode lead is implanted along a linear trajectory linking the DMN and the VL-PAG across the LH and the PC.

As a first example, the plurality of evenly spaced electrodes may include eight electrodes, each having a length of around 1.5 mm, with a spacing of about 1.5 mm between adjacent electrodes. As a second example, the plurality of evenly spaced electrodes may include twelve electrodes, each having a length of around 1.5 mm, with a spacing of about 0.5 mm between adjacent electrodes. Of course, other examples with different numbers of electrodes and different dimensions are also possible. The second example may provide a higher spatial resolution than the first example, due to the increased number of electrodes per unit length.

The apparatus may further include a proximal electrode (which may also be referred to as a further electrode) which is arranged to apply a neuromodulation signal to the DACC and/or CC. In this manner, a neuromodulation signal may be applied to the DACC and/or CC.

A length and position of the proximal electrode may determine whether the electrode can apply a neuromodulation signal to one or both of the DACC and CC.

In some embodiments, the proximal electrode may be provided separately from the electrode lead, e.g. the proximal electrode may be on a further electrode lead or on a guide tube of the apparatus.

In some embodiments, the proximal electrode may be disposed on the electrode lead. In this manner, a neuromodulation signal may be applied to the DACC and/or CC via the electrode lead. Thus, the electrode lead may enable combined neurostimulation of one or more of the DMN, LH, PC, VL-PAG DACC and CC.

The proximal electrode may be similar to the electrodes in the plurality of electrodes described above, e.g. it may be ring-shaped (e.g. cylindrical) or it may be a directional electrode.

The proximal electrode may be spaced apart from the plurality of electrodes in a longitudinal direction, e.g. so that it may be positioned adjacent to the DACC and/or CC when the electrode lead is implanted into the subject's brain. In particular, the proximal electrode may be located closer to a proximal end of the electrode lead than the plurality of electrodes which are on the distal portion of the electrode lead.

The proximal electrode may be longitudinally spaced from the plurality of electrodes by a distance of about 5-15 mm.

A spacer, e.g. made of an electrically insulating material, may be disposed between the proximal electrode and the plurality of electrodes.

The spacer may have a length of approximately 5-15 mm, i.e. a distance between the proximal electrode and the plurality of electrodes may be between 5-15 mm. The exact position and dimensions of the proximal electrode may be set based on a location of the DACC and/or CC in the subject's brain, to ensure that the DACC and/or CC may be effectively stimulated.

Each of the electrodes in the plurality of electrodes may have a first length, and the proximal electrode may have a second, longer length. Thus, the proximal electrode may be longer than the other electrodes. This may facilitate applying a neuromodulation signal to the DACC, as the inventors have found that a distance across the lateral ventricle between the DACC and the DMN may vary from subject to subject. Thus, having a longer proximal electrode may compensate for the variation in position of the DACC from subject to subject, so that the DACC and/or CC can be effectively stimulated with the proximal electrode.

The length of the electrodes in the plurality of electrodes, i.e. the first length, may preferably be around 1.5 mm, as discussed above.

The second length may be between 10-30 mm. Such a length of the proximal electrode may ensure that the DACC and/or CC can be effectively stimulated via the proximal electrode, despite variations in the distance across the lateral ventricle between subjects. In particular, the inventors have found that the distance across the lateral ventricle may be between 9-20 mm for different subjects. Thus, by providing the proximal electrode with a length between 10-30 mm, it may be possible to stimulate the DACC and/or CC in different subjects. Preferably, the second length may be between 20-30 mm.

In some embodiments, the apparatus may further include a guide tube for insertion into the patient's brain, the guide tube including a hollow tube defining a longitudinal channel in which the electrode lead is receivable.

A length of the hollow tube may be arranged such that, when the electrode lead is received in the longitudinal channel, the distal portion of the electrode lead protrudes from a distal opening of the hollow tube.

The guide tube may serve to facilitate implantation of the electrode lead into the subject's brain, as it may ensure that the electrode lead follows the correct trajectory during insertion. In particular, the guide tube may facilitate transventricular implantation of the electrode lead, i.e. implantation of the electrode lead via the lateral ventricle.

The hollow tube may have a generally cylindrical shape, with the longitudinal channel extending along a length of the hollow tube.

The longitudinal channel may be dimensioned to receive the electrode lead, e.g. a diameter of the longitudinal channel may be slightly larger than an outer diameter of the electrode lead.

The hollow tube may be made of any suitable insulating biocompatible material, e.g. a biocompatible plastic material (e.g. polycarbonate urethane). Preferably the material of the hollow tube is rigid, to facilitate insertion of the hollow tube into the subject's brain, and to prevent movement of the guide tube after insertion into the subject's brain.

The guide tube may be inserted into the subject's brain by first introducing a guide rod into the subject's brain along a desired trajectory, and then sliding the hollow tube over the guide rod. The guide rod may then be withdrawn from the hollow tube, and the electrode lead may be inserted into the subject's brain via the guide tube to a desired depth, i.e. so that the distal portion of the electrode lead reaches a target location in the subject's brain.

The guide rod may typically be manufactured from a radio opaque material, to facilitate visualisation of the guide rod under computed tomography (CT) or magnetic resonance imaging (MRI).

A length of the hollow tube may be shorter than a length of the electrode lead, such that the distal portion of the electrode lead protrudes from the distal opening of the hollow tube when the electrode lead is inserted into the guide tube. In this manner, when the electrode lead is inserted into the guide tube, the plurality of electrodes on the distal portion of the electrode lead may be exposed, so that they can apply a neuromodulation signal to target brain tissue.

A length of the hollow tube may be arranged to span a distance between the subject's skull and slightly below the lateral ventricle (e.g. a few millimetres below the lateral ventricle). The hollow tube may be cut to a desired length prior to insertion into the patient's brain, e.g. based on measurements of the subject's brain.

Where the electrode lead includes a proximal electrode, the guide tube may be configured to enable transmission of the neuromodulation signal from the proximal electrode to an outside of the hollow tube when the electrode lead is received in the longitudinal channel of the hollow tube.

When the electrode lead is received in the longitudinal channel, the proximal electrode may be located in the longitudinal channel. Enabling the hollow tube to transmit the neuromodulation single from the proximal electrode to the outside of the hollow tube may thus enable the neuromodulation signal to be applied to the DACC and/or CC. In this manner, the hollow tube need not be made shorter in order to expose the proximal electrode, which could compromise the guide tube's ability to guide the electrode lead along the desired trajectory. Thus, the guide tube may serve to accurately guide the electrode lead along the desired trajectory, whilst enabling the DACC and/or CC to be stimulated via the proximal electrode on the electrode lead.

In some embodiments, the guide tube may include a window formed in a sidewall of the hollow tube, the window being arranged to expose the proximal electrode to an outside of the hollow tube when the electrode lead is received in the longitudinal channel of the hollow tube. Thus, the window in the sidewall of the hollow tube may enable transmission of the neuromodulation signal from the proximal electrode to the outside of the hollow tube.

When the electrode lead is inserted into the hollow tube, the proximal electrode may be exposed via the window so that it can be used to apply a neuromodulation signal to the DACC and/or CC. Providing a window in the sidewall of the hollow tube for the proximal electrode may enable the proximal electrode to be exposed, without having to shorten the length of the hollow tube. As a result, the guide tube may enable accurate placement of the distal portion of the electrode lead, whilst exposing the proximal electrode through the window. The window may be arranged to expose all or a portion of the proximal electrode.

A length of the window in the sidewall of the hollow tube may be shorter than a length of the proximal electrode (e.g. the second length discussed above). As a result, only a portion of the proximal electrode may be exposed via the window. The length and position of the window may be determined based on a location of the DACC in the subject's brain. As a result, the portion of the proximal electrode that is exposed via the window may be proximal to the DACC so that a neuromodulation signal can be applied to the DACC and/or CC via the proximal electrode.

As the proximal electrode may be relatively long (e.g. between 10-25 mm), it may be beneficial to only expose a shorter portion of the proximal electrode, in order to avoid stimulating regions away from the DACC with the proximal electrode.

The window may for example be cut in the sidewall of the hollow tube (e.g. via laser cutting), or it may be integrally formed as part of the hollow tube (e.g. via a moulding or 3D printing process).

The window may have a length of 10-25 mm, for example.

The guide tube may include a marker for indicating a direction in which the window is facing, i.e. for indicating an orientation of the window.

The marker may be arranged on the guide tube such that it is visible when the guide tube is inserted into the subject's brain.

The marker may serve to inform a user (e.g. surgeon) of the direction in which the window is facing, so that the user may insert the guide tube in the correct orientation, e.g. so that the window faces towards the DACC and/or CC. For example, the marker may be disposed on a cap of the guide tube, so that it may be visible to the user during insertion of the guide tube into the user's brain.

The window may be arranged to face towards the DACC and/or CC when the guide tube is inserted into the subject's brain. This may serve to direct the neuromodulation signal from the proximal electrode towards the DACC, to ensure effective stimulation of the DACC.

The window may be formed on a side of the hollow tube, so that the window is arranged to face towards the DACC when in use. In other words, the window may only cover a portion of the circumference of the hollow tube, i.e. it does not extend all the way around the circumference of the hollow tube. For example, the window may have an opening angle between 10° and 90° about a longitudinal axis of the hollow tube.

In some examples, the window may comprise two or more apertures formed in the hollow tube. Forming the window as two or more apertures (e.g. as opposed to a single larger aperture) may serve to improve the rigidity of the hollow tube, which may facilitate insertion of the guide tube into the subject's brain. For example, the window may be formed by an array of longitudinally spaced apertures in the sidewall of the hollow tube.

In some embodiments, the guide tube may include an outer electrode at an outer surface of the hollow tube. The outer electrode may be used for applying a neuromodulation signal to target brain tissue. In this manner, a neuromodulation signal may be applied to target brain tissue via the outer electrode of the guide tube. Thus, neuromodulation signals may be applied via both the electrode lead and the guide tube.

The outer electrode is arranged at the outer surface of the hollow tube, so that it may come into contact with target brain tissue.

The outer electrode may be made of a conductive material, e.g. platinum-iridium.

The outer electrode may be arranged to apply a neuromodulation signal to the DACC and/or CC.

As an example, the outer electrode may include a mesh electrode on the outer surface of the hollow tube. The mesh electrode may, for example, be in the form of a meshed metallic sleeve disposed on the outer surface of the hollow tube.

As another example, the outer electrode may include an electrode which is embedded in a material (e.g. plastic material) forming the sidewall of the hollow tube, the sidewall of the hollow tube including a window formed therein for exposing a portion of the electrode.

In some cases, the outer electrode may extend around a circumference of the guide tube, e.g. it may have a generally cylindrical shape. In other cases, the outer electrode may be arranged to provide directional stimulation, e.g. where it is exposed via a window in the material forming the sidewall of the hollow tube. In such cases, the guide tube may include an indicator for indicating a direction in which the outer electrode faces, e.g. the indicator may be on a cap of the guide tube.

The outer electrode may be electrically connected to the controller via a connecting lead extending through the hollow tube. In this manner, a neuromodulation signal generated by the controller may be directly conveyed to the outer electrode on the guide tube via the connecting lead. Thus, it may not be necessary to provide a proximal electrode on the electrode lead. For example, the connecting lead may be in the form of a fine wire which is embedded in a material forming the hollow tube. Alternatively, the connecting lead may be disposed within the longitudinal channel of the hollow tube.

Where the electrode lead includes a proximal electrode, the outer electrode may be configured for electrical connection to the proximal electrode when the electrode lead is received in the longitudinal channel of the hollow tube. Then, when the electrode lead is received in the longitudinal channel in the hollow tube, the proximal electrode on the electrode lead may be electrically connected to the outer electrode on the guide tube. As a result, a neuromodulation signal applied to the proximal electrode may be transmitted to the outer electrode, so that the outer electrode may apply the neuromodulation signal to surrounding target tissue, e.g. to the DACC. The outer electrode may thus be used as an alternative to the window, in order to apply a neuromodulation signal to the DACC when using a guide tube.

By providing an outer electrode on the guide tube which is arranged for electrical connection to the proximal electrode, it may be possible to reduce a length of the proximal electrode, as the proximal electrode need only be long enough to provide a reliable connection to the outer electrode when the electrode lead is received in the longitudinal channel of the hollow tube.

Various mechanisms may be used to electrically connect the outer electrode to the proximal electrode when the electrode lead is received in the longitudinal channel of the hollow tube. For example, a connecting portion of the outer electrode may be disposed (e.g. exposed) in the longitudinal channel, such that the proximal electrode may come into contact with the connecting portion of the outer electrode when the electrode lead is received in the longitudinal channel.

The connecting portion of the outer electrode may be arranged to form a slidable electrical connection with the proximal electrode, to enable the electrode to be inserted through the longitudinal channel.

The outer electrode may be a ring-shaped electrode, i.e. it may extend around a circumference of the hollow tube.

Alternatively, the outer electrode may be configured to apply the neuromodulation signal in a particular direction, e.g. the outer electrode may extend around only a portion of the circumference of the hollow tube. In particular, the outer electrode may be arranged to face towards the DACC when it is inserted into the subject's brain.

In such a case, the guide tube may include a marker (e.g. on the cap of the guide tube) indicating a direction in which the outer electrode is facing. In this manner, a user may ensure that the outer electrode is correctly oriented, to enable stimulation of the DACC.

The guide tube may comprise a cap which is securable to a hole (e.g. burr hole). The cap may thus serve to secure the guide tube to the subject's skull. For example, the cap may include a threaded outer surface, so that it may be screwed into the hole in the subject's skull. This may also facilitate removing the guide tube at a later date.

In some embodiments, the cap may be secured to a proximal end of the hollow tube. The cap may then include an inlet for inserting the electrode lead into the longitudinal channel of the hollow tube.

In other embodiments, the cap may be separate from the hollow tube. The cap may include a passageway through which the hollow tube is insertable, e.g. the hollow tube may be slidably insertable through the passageway. In other words, when the hollow tube is inserted into the passageway in the cap, the cap may be movable relative to the hollow tube along a longitudinal direction of the hollow tube.

In this manner, the hollow tube may be inserted into the subject's brain via the passageway in the cap. A position of the hollow tube relative to the cap may be adjustable, e.g. by inserting a desired length of the hollow tube through the passageway in the cap. This may enable a user to adjust a length of the hollow tube which is inserted into the subject's brain.

The passageway in the cap may be arranged to form a sliding seal around the hollow tube when the hollow tube is inserted through the passageway, in order to prevent leakage via the cap.

The ability to adjust a length of the hollow tube that is inserted through the passageway in the cap may be particularly beneficial where the hollow tube includes a window or an outer electrode, as it may enable the user (e.g. surgeon) to ensure that the window or outer electrode is at an appropriate depth in the subject's brain. In particular, it may enable the user to ensure that the window or outer electrode are positioned to enable application of a neuromodulation signal to the DACC and/or CC.

The guide tube may include an indicator for indicating a length of the hollow tube which has been inserted through the passage way in the cap, e.g. in the form of a graduated line along a side of the hollow tube. The indicator may be arranged to indicate a distance between the cap and the window or outer electrode.

Additionally or alternatively, the hollow tube may include an indicator for indicating an orientation of the window or outer electrode.

The guide tube may further comprise a first limiter, the first limiter being secured to a proximal portion of the hollow tube, and arranged to abut against the cap when a pre-determined length of the hollow tube is inserted through the passageway. The first limiter may serve to ensure that only the predetermined length of hollow tube is inserted into the subject's brain via the passageway in the cap. In this manner, it may be possible to ensure that the hollow tube is inserted into the subject's brain to a desired depth. The pre-determined length may be determined by a position at which the first limiter is secured to the proximal portion of the hollow tube. In use, the distal portion of the hollow tube may be inserted through the passageway in the cap, until the first limiter on the proximal portion of the hollow tube abuts against the cap, thus preventing further insertion of the hollow tube through the passageway in the cap.

A position of the first limiter on the proximal portion of the hollow tube may be adjustable in order to set the pre-determined length of the hollow tube. The first limiter may be provided separately from the guide tube, i.e. it may be securable to the proximal portion of the hollow tube. In some cases, the first limiter may be removably securable to the proximal portion of the hollow tube.

The apparatus may further comprise a second limiter, the second limiter being secured to a proximal portion of the electrode lead, and arranged to abut against a proximal end of the guide tube when a pre-determined length of the electrode lead protrudes from the distal opening of the hollow tube.

The second limiter may serve to ensure that only the pre-determined length of the electrode lead protrudes from the distal opening of the hollow tube. In this manner, it may be possible to ensure that the electrode lead is inserted into the subject's brain to a desired depth, e.g. so that the distal portion of the electrode lead is appropriately positioned for applying the one or more neuromodulation signals.

The pre-determined length may be determined by a position at which the second limiter is secured to the proximal portion of the electrode lead.

In use, the distal portion of the electrode lead may be inserted through the longitudinal channel of the hollow tube, until the second limiter on the proximal portion of the electrode lead abuts against the cap, thus preventing further insertion of the electrode lead through the hollow tube.

A position of the second limiter on the proximal portion of the electrode lead may be adjustable in order to set the pre-determined length of the electrode lead. The first limiter may be provided separately from the electrode lead, i.e. it may be securable to the proximal portion of the hollow tube. In some cases, the first limiter may be removably securable to the proximal portion of the hollow tube.

In some embodiments, the apparatus may further comprise a sensor arranged to detect a physiological parameter of the subject and to generate an output signal related to the detected physiological parameter, wherein the controller is configured to adjust at least one of the one or more neuromodulation signals based on the output signal from the sensor.

In this manner, the physiological parameter may be used as feedback for adjusting the neuromodulation signals. This may enable more accurate and effective neurostimulation of the brain, as the neuromodulation signals may be adjusted based on the subject's response to the signals.

For example, the physiological parameter may include one or more of the subject's blood pressure, blood flow, cerebral blood flow, intracranial pressure.

Where neuromodulation signals are applied to the VL-PAG, the DACC and/or CC, the neuromodulation signals applied to the VL-PAG, the DACC and/or CC may be adjusted based on the detected physiological parameter.

Adjusting a neuromodulation signal may involve adjusting one or more parameters of the neuromodulation signal, such as frequency, pulse width and pulse amplitude. In some cases, a set point may be associated with the physiological parameter, and the neuromodulation signal may be adjusted until the set point is reached.

Various types of sensors may be used to detect blood pressure and/or blood flow. As an effect of neurostimulation of the subject's brain may be to enhance brain perfusion, changes in blood pressure and/or blood flow may serve as an indication of effectiveness of the treatment.

For example, the sensor may include a wearable sensor configured to measure blood pressure and/or blood flow. The wearable sensor may be in the form of a sensor wearable on the user's wrist (e.g. as a wrist watch).

In some cases, the sensor may include an implantable sensor, which is arranged to detect blood pressure and/or blood flow. For example, the implantable sensor may be arranged to be implanted over the carotid bifurcation, in the carotid sinus or in the aortic arch.

Where the physiological parameter is intracranial pressure, the sensor may be in the form of a pressure sensor that is implantable beneath the subject's skull.

In some cases, the pressure sensor may be incorporated into the electrode lead, or it may be incorporated into the guide tube. This may avoid having to implant the sensor separately from the electrode lead and guide tube. Similarly to blood pressure and/or blood flow, intracranial pressure may serve as an indicator of effectiveness of the treatment.

In some cases, the sensor may be incorporated in the generator. The accelerometer in the device which would ordinarily serve to detect changes in the individuals position and motion, may be optimised to sense changes in motion of the surrounding skull or underlying dura secondary to brain pulse and calibrated to cerebral blood flow, and also sense changes in heart rate.

The sensor may be communicatively coupled to the controller, e.g. via a wired or wireless connection, so that the output signal from the sensor can be transmitted to the controller. Upon receiving the output signal from the sensor, the controller may compare the detected physiological parameter to a predetermined set point for the physiological parameter, and adjust at least one of the one or more of the neuromodulation signals, for example to try to change the detected physiological parameter to be less than, the same as, or more than the set point.

In some embodiments, the apparatus may further comprise an external power supply, the external power supply including a transmitter for wirelessly transmitting power to the controller. In this manner, there does not need to be a wired connection between the external power supply and the controller. Thus, during use, the external power supply may be worn by the subject so that it is in proximity to the controller. Then, after use, the external power supply may easily be removed. This may facilitate charging of the external power supply, as well as improve comfort for the user when the apparatus is not in use, as the external power supply can be removed. This may be particularly beneficial in cases where neurostimulation is only to be performed during short intervals. The external power supply may include a power source, such as a battery (e.g. rechargeable battery).

Power may be transmitted from the external power source's transmitter to the controller via inductive coupling between the transmitter and the controller. For example, the transmitter may include a transmitter coil, and the controller may include a receiver coil, the transmitter coil and receiver coil being inductively couplable so that power may be transferred from the transmitter to the controller.

The apparatus may further include a wearable cap configured to hold the transmitter in proximity of the controller. In this manner, the subject may wear the cap to hold the transmitter in proximity of the controller to power the controller.

The cap may include a pocket arranged to hold the transmitter. The cap may be arranged to hold the transmitter above the controller, which may ensure effective power transmission from the transmitter to the controller.

The apparatus may further include one or more stimulation electrodes for applying one or more stimulation signals to a carotid body and/or a carotid baroreceptor in the subject.

Such an apparatus may be considered as an independent aspect of the invention. More generally, in such an independent aspect, the apparatus may include an electrode lead for applying one or more neuromodulation signals to one or more targets in the subject's brain, without necessarily being limited to the targets discussed above. Thus, an independent aspect of the invention may provide a system comprising an apparatus for applying one or more neuromodulation signals to one or more targets in the subject's brain; and a stimulation electrode for applying a stimulation signal to a carotid body and/or a carotid baroreceptor in the subject.

The one or more stimulation electrodes may be arranged to apply stimulation signals to one or carotid bodies and/or carotid baroreceptors.

The one or more stimulation electrodes may be disposed on an implantable lead which is arranged for implantation into the subject, for example as described in US 2015/0112359 A1. The stimulation signals applied via the stimulation electrodes may be pulsed RF signals. A pulsed RF signal may serve to stimulate the carotid body and/or carotid baroreceptor, without heating the tissues to a temperature at which they would be ablated.

The controller may be configured to generate the one or more stimulation signals applied via the one or more stimulation electrodes. In this manner, the controller may be configured to generate the one or more neuromodulation signals applied by the plurality of electrodes on the electrode lead, and the one or more stimulation signals applied by the one or more stimulation electrodes.

In such a case, the one or more stimulation electrodes may be connected to the controller e.g. via connecting wires.

Where the one or more electrodes are disposed on an implantable lead, the implantable lead may be connected to the controller, so that the one or more stimulation signals may be transmitted to the one or more stimulation electrodes.

Generating both the neuromodulation signals and the stimulation signals with a single controller may facilitate coordination of application of neuromodulation signals and stimulation signals to their respective targets. This may also reduce the number of components in the apparatus.

Alternatively, a separate signal generator may be provided to generate the one or more stimulation signals. In such a case, the controller and the signal generator may be in wired or wireless communication with each other. This may enable application of the one or more neuromodulation signals and the one or more stimulation signals to be coordinated.

The guide tube described as part of the second aspect of the invention may form independent aspects of the invention.

Thus, according to a third aspect of the invention, there is provided a guide tube for insertion into a subject's brain, the guide tube comprising a hollow tube defining a longitudinal channel in which an electrode lead is receivable; wherein the guide tube includes a window formed in a sidewall of the hollow tube, the window being arranged to expose a proximal electrode on the electrode lead to an outside of the hollow tube when the electrode lead is received in the longitudinal channel of the hollow tube.

Features of the guide tube described in relation to the second aspect of the invention may be shared with the guide tube of the third aspect of the invention, and are therefore not repeated.

The guide tube may include a window formed in a sidewall of the hollow tube, the window being arranged to expose the proximal electrode to the outside of the hollow tube when the electrode lead is received in the longitudinal channel of the hollow tube.

A length of the window may be shorter than a length of the proximal electrode.

The guide tube may include a marker for indicating a direction in which the window is facing.

The window may comprise two or more apertures in the sidewall of the hollow tube.

According to a fourth aspect of the invention, there is provided a guide tube for insertion into a subject's brain, the guide tube comprising a hollow tube defining a longitudinal channel in which an electrode lead is receivable; wherein the guide tube includes an outer electrode on an outer surface of the hollow tube.

Features of the guide tube described in relation to the second aspect of the invention may be shared with the guide tube of the third aspect of the invention, and are therefore not repeated.

In some embodiments, the guide tube may further comprise a connecting lead extending through the hollow tube for connecting the outer electrode to a controller.

In other embodiments, the outer electrode may be configured for electrical connection to a proximal electrode on the electrode lead when the electrode lead is received in the longitudinal channel of the hollow tube.

The guide tube of the third or fourth aspect of the invention may further comprise a cap that is securable to a hole in the subject's skull, the cap including a passageway through which the hollow tube is insertable to insert the hollow tube into the subject's brain.

The guide tube of the third or fourth aspect of the invention may further comprise further comprising a first limiter secured to a proximal portion of the hollow tube, the first limiter being arranged to abut against the cap when a pre-determined length of the hollow tube is inserted through the passageway.

Herein, the term "distal" may refer to an end or a portion of a component (e.g. the electrode lead or guide tube) which, in use, is located deeper within a subject's brain. For example, the distal portion of the electrode lead may be a portion of the electrode lead which is deepest in the subject's brain following implantation of the electrode lead into the subject's brain.

Herein, the term "proximal" may refer to an end or a portion of a component (e.g. the electrode lead or guide tube) which, in use, is located closer to the controller, i.e. closer to the user's skull.

Herein a "length" of a component (e.g. of an electrode) may refers to a length of that component along a longitudinal direction of the electrode lead or hollow tube of the guide tube.

BRIEF DESCRIPTION OF THE DRAWINGS

Embodiments of the invention are discussed below with reference to the accompanying drawings, in which:

FIG. 2b is a schematic diagram illustrating a configuration where the electrode lead of FIG. 1 is received in the guide tube of FIG. 2a;

FIG. 3a is a schematic diagram of a guide tube according to an embodiment of the invention;

FIG. 3b is a schematic diagram of an apparatus according to an embodiment of the invention;

FIG. 4b is an expanded cross-sectional view of a portion of the guide tube of FIG. 4a;

FIG. 6b is a cross-sectional view of a portion of the apparatus of FIG. 6a;

FIG. 6c is a top view of a portion of the apparatus of 6a;

FIG. 7a is a cross-sectional view of an apparatus according to an embodiment of the invention;

FIG. 7b is a schematic diagram of the apparatus of FIG. 7a;

FIG. 9 is a schematic diagram showing an apparatus according to an embodiment of the invention in use on a subject;

FIG. 10b is a side view of a subject's head, indicating a cross-sectional line corresponding to the cross-sectional view shown in FIG. 10a;

DETAILED DESCRIPTION; FURTHER OPTIONS AND PREFERENCES

Figure 1:
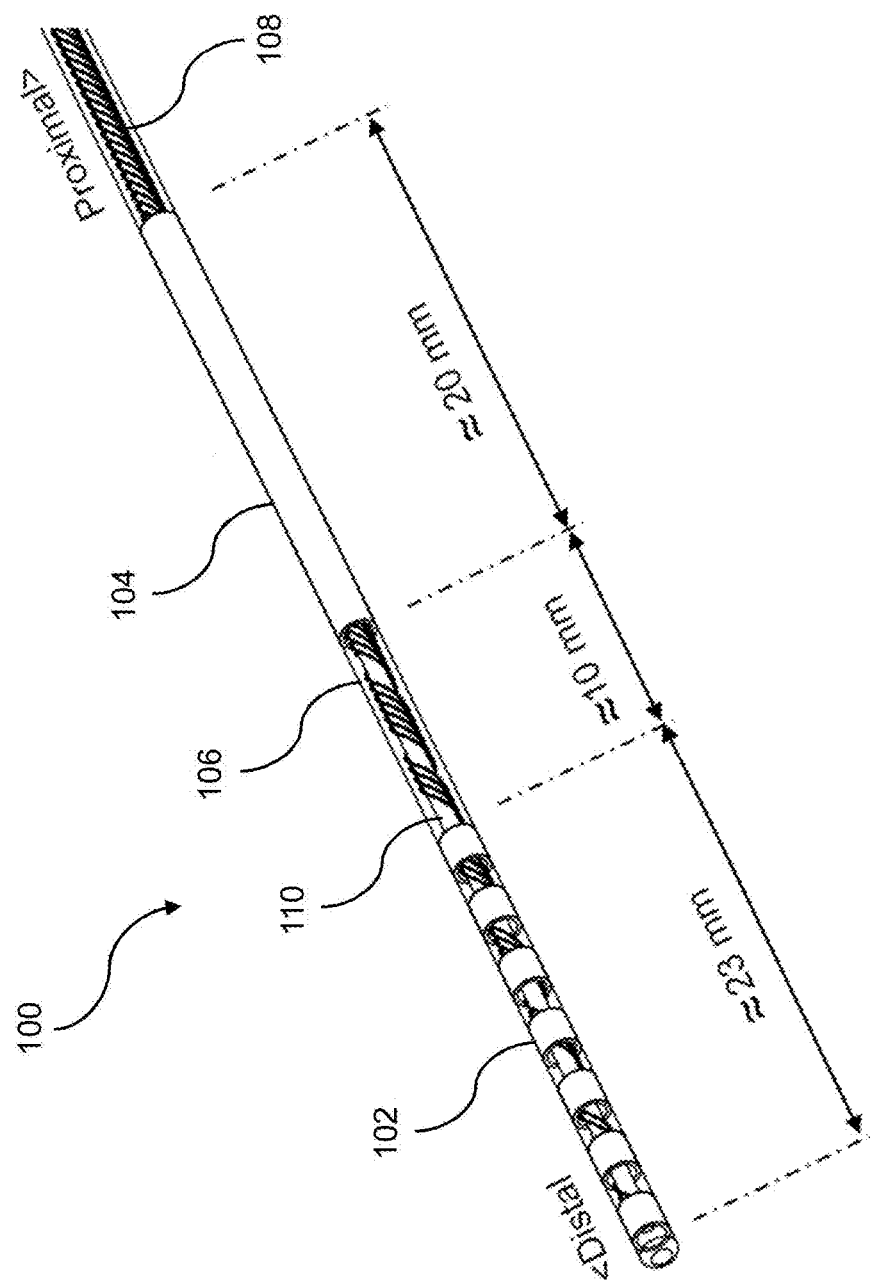
FIG. 1 is a schematic diagram of an electrode lead that may form part of an apparatus according to an embodiment of the invention.

FIG. 1 is a schematic diagram of an electrode lead 100 that may form part of an apparatus according to an embodiment of the invention. The electrode lead 100 is arranged for insertion into a subject's brain, along a trajectory linking the dorsomedial nucleus (DMN) and the ventrolateral periaqueductal gray (VL-PAG) across the lateral habenula (LH) and the posterior commissure (PC). The electrode lead 100 is configured to apply one or more neuromodulation signals to targets along the implantation trajectory of the electrode lead, including the DMN, LH, PC and VL-PAG. Furthermore, the electrode lead 100 is configured to apply a neuromodulation signal to the dorsal anterior cingulate cortex (DACC) and/or the corpus callosum (CC). A preferred implantation trajectory of the electrode lead 100 into the subject's brain is described below in relation to FIGS. 10 to 13.

The electrode lead 100 is in the form of an elongate, cylindrical cable having a plurality of electrodes 102 at a distal portion of the electrode lead 100. The plurality of electrodes 102 includes seven evenly spaced electrodes. Each electrode 102 has a cylindrical shape, and has a length of approximately 1.7 mm, with a spacing of approximately 1.7 mm between adjacent electrodes. In this manner, a total length spanned by the plurality of electrodes 102 is approximately 23 mm. The plurality of electrodes 102 may thus enable the DMN and VL-PAG, as well as targets located between the DMN and the VL-PAG (e.g. the LH and PC) to be stimulated via the electrodes 102. By providing the plurality of electrodes as an array of regularly spaced electrodes, it may be possible to accommodate variations in distances between targets for different subjects.

In other examples, the plurality of electrodes 102 may include a different number of electrodes, and the electrodes 102 may have different dimensions, e.g. depending on the specific targets to be treated. Generally, the plurality of electrodes 102 may span a length between 20-30 mm, as this may correspond to a typical distance between the DMN and VL-PAG for most subjects.

The electrode lead 100 further includes a proximal electrode 104 which is spaced from the plurality of electrodes 102. The proximal electrode 104 is spaced from the plurality of electrodes 102 by a distance of approximately 10 mm, such that the proximal electrode is located closer to a proximal end of the electrode lead 100 than the plurality of electrodes 102.

In other examples, the proximal electrode 104 may be spaced from the plurality of electrodes 102 by a distance of approximately 5-15 mm.

A spacer 106 may be provided between the proximal electrode 104 and the plurality of electrodes 102.

The proximal electrode 104 has a cylindrical shape, and has a length of approximately 20 mm. In other examples, the proximal electrode 104 may have a length between 15-30 mm.

The proximal electrode 104 is arranged to apply a neuromodulation signal to the DACC and/or CC. The length of the proximal electrode 104 may serve to compensate for variations in a position of the DACC between subjects, to ensure that a neuromodulation signal may be applied to the DACC and/or CC.

The electrode lead 100 includes a plurality of wires 108 extending within the electrode lead 100. Each of the plurality of electrodes 102 and the proximal electrode 104 is electrically connected to a respective one of the plurality of wires 108. In this manner, a neuromodulation signal may be applied to each of the electrodes 102 and the proximal electrode 104 via a corresponding wire. Each of the electrodes 102 and the proximal electrode may be electrically isolated from one another, so that separate neuromodulation signals may be applied to each individual electrode. In this manner, multiple targets may be individually stimulated with the electrode lead 100.

Each of the electrodes 102 and the proximal electrode 104 is exposed on an outer surface of the electrode lead 100, so that they may come into contact with target brain tissue when the electrode lead 100 is inserted into the brain.

The plurality of wires 108 may be wrapped around or carried by an inner core 110 of the electrode lead 100. The inner core 110 may be made of a rigid material, to confer rigidity to the electrode lead 100 and facilitate insertion of the electrode lead into the subject's brain.

A proximal end of the electrode lead may be connected to a controller (not shown), the controller being configured to generate one or more neuromodulation signals to be applied by the plurality of electrodes 102 and the proximal electrode 104.

In particular, the wires 108 may be electrically connected to the controller, so that neuromodulation signals generated by the controller may be conveyed to the electrodes 102 and the proximal electrode 104 via the wires 108.

Each of the plurality of wires 108 may be connected to a respective channel in the controller, so that separate neuromodulation signals may be applied via each of the plurality of electrodes 102 and the proximal electrode 104.

The controller may, for example, be in the form of an implantable pulse generator (IPG).

Figure 2A:
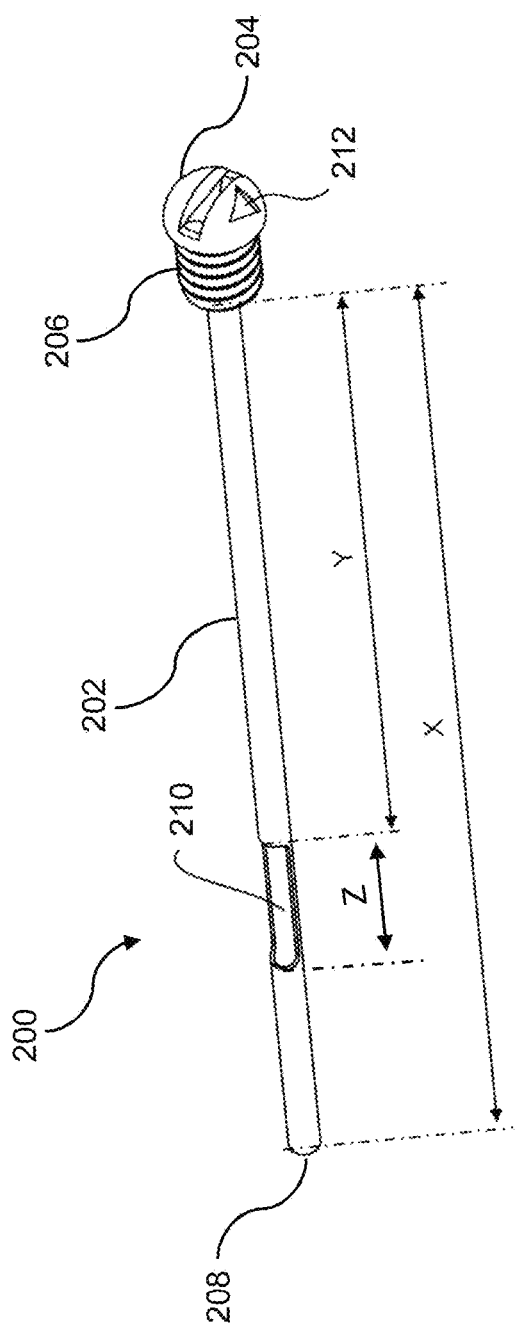
FIG. 2a is a schematic diagram of a guide tube according to an embodiment of the invention.

FIG. 2*a* shows a schematic diagram of a guide tube 200 according to an embodiment of the invention. The guide tube 200 may form part of an apparatus according to an embodiment of the invention.

The guide tube 200 includes a hollow tube 204 which defines a longitudinal channel extending therethrough, and in which an electrode lead (e.g. electrode lead 100) is receivable. The guide tube 200 includes a cap 204 disposed at a proximal end of the hollow tube 202.

The cap 204 may be fixed to the proximal end of the hollow tube 202.

The cap 204 includes an inlet for inserting the electrode lead into the longitudinal channel in the hollow tube 202. Thus, the electrode lead 100 may be inserted into the subject's brain via the guide tube 200. The hollow tube 202 may serve to guide the electrode lead 100 along a desired trajectory within the subject's brain, to facilitate implantation of the electrode lead 100.

The cap 204 further includes a threaded outer surface 206, so that it may be screwed into an insertion hole (e.g. burr hole) formed in the subject's skull. In this manner, the guide tube 200 may be inserted into the subject's brain via an insertion hole in the skull, and secured to the skull via the threaded outer surface 206. The hollow tube 202 may be made of a rigid plastic material, to facilitate insertion of the hollow tube 202 into the subject's brain.

A length of the hollow tube 202 (shown as X in FIG. 2*a*) is arranged such that, when the electrode lead 100 is inserted into the longitudinal channel in the hollow tube 202, the distal portion of the electrode lead comprising the plurality of electrodes 102 protrudes from a distal opening 208 of the hollow tube 202. In this manner, when the electrode lead 100 is received in the longitudinal channel in the hollow tube 202, the plurality of electrodes 102 on the electrode lead 100 are exposed so that neuromodulation signals may be applied to surrounding brain tissue via the plurality of electrodes 102.

The hollow tube 202 may be cut to an appropriate length prior to insertion into the subject's brain, e.g. based on measured dimensions of the subject's brain. In particular, the length X of the hollow tube 202 may correspond to a distance between the subject's skull and a few millimetres below the lateral ventricle. This may facilitate transventricular implantation of the electrode lead. For example, the length X may be between 45 and 65 mm.

The guide tube 200 includes a window 210 formed in a sidewall of hollow tube 202. The window 210 is arranged such that, when the electrode lead 100 is received in the longitudinal channel in the hollow tube, a portion of the proximal electrode 104 is exposed via the window 210.

A length of the window 210 (shown as Z in FIG. 2*a*) is shorter than a length of the proximal electrode 104, such that the portion of the proximal electrode 104 that is exposed via the window 210 is shorter than the length of the proximal electrode 104. So, in the example of FIG. 1, where the proximal electrode has a length of approximately 20 mm, the window 210 may have a length of less than 20 mm, e.g. 10 mm or 5 mm. By making the window 210 shorter than the proximal electrode 104, it is possible to ensure that the proximal electrode 104 only applies a neuromodulation signal to brain tissue in a target region around the window 210, rather than along the entire length of the proximal electrode 104. This may avoid stimulating brain tissue away from the target region.

As mentioned above, the window 210 may have a length of 10-25 mm, for example.

The window 210 in the hollow tube 202 is positioned such that it is aligned with the DACC when the guide tube is inserted into the subject's brain. In this manner, the portion of the proximal electrode 104 that is exposed via the window 210 may be used to apply a neuromodulation signal to the DACC and/or CC.

In particular, a distance between the cap 204 and the window 210 (shown as Y in FIG. 2*a*) may be set such that the window 210 is positioned adjacent to the DACC. In order to account for variations in anatomy between subjects, guide tubes having different values of Y may be provided.

For example, the distance between the cap 204 and the window 210 (shown as Y in FIG. 2*a*) may be 20-35 mm.

The window 210 is formed in the sidewall of the hollow tube 202 so that it faces in a radial direction. In this manner, when the electrode lead 100 is disposed in the longitudinal channel in the hollow tube 202, an orientation of the hollow tube 202 relative to the electrode lead 100 may determine a direction in which the proximal electrode 104 can apply a neuromodulation signal. The cap 204 of the guide tube 200 includes a marker 212 (or indicator) in the form of an arrow, to indicate a direction in which the window 210 is facing. In this manner, a user (e.g. surgeon), may ensure that the window is oriented in a correct direction when inserting the guide tube 200 into the subject's brain. In particular, the marker 212 may serve to ensure that the window 210 faces towards the DACC when the guide tube is inserted into the subject's brain.

Figure 2B:
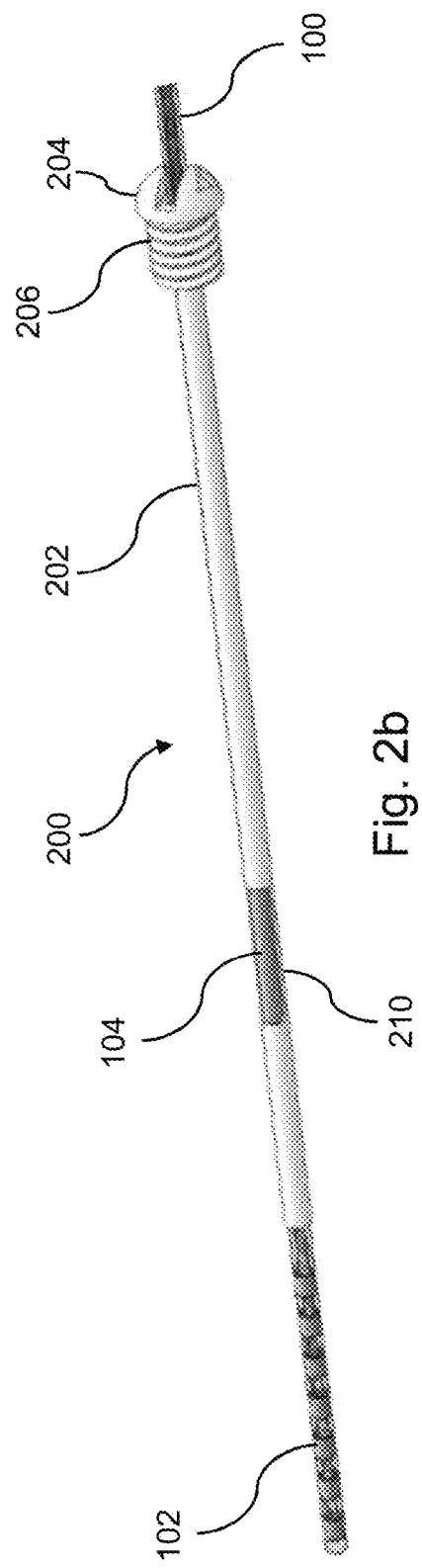

FIG. 2*b* illustrates a configuration where the electrode lead 100 is received in the longitudinal channel in the hollow tube 202 of the guide tube 200. As can be seen in FIG. 2*b*, in this configuration, the distal portion of the electrode lead 100 comprising the plurality of electrodes 102 protrudes from the distal opening 208 of the hollow tube 202. Moreover, a portion of the proximal electrode 104 is exposed via the window 210 in the sidewall of the hollow tube 202. A proximal end of the electrode lead 100 extends through the inlet in the cap 204 of the guide tube 200, so that the electrode lead 100 may be connected to a controller (not shown).

FIG. 3a shows a schematic diagram of a guide tube 300 according to another embodiment of the invention. The guide tube 300 may form part of an apparatus according to an embodiment of the invention. The guide tube 300 is similar to guide tube 200 described above, however the window is configured differently. Accordingly, features of guide tube 300 corresponding to those described in relation to guide tube 200 are indicated in FIG. 3a with the same reference numerals as in FIG. 2a, and are not described again.

The guide tube 300 includes a window 310 formed in a sidewall of the hollow tube 202. The window 310 comprises three apertures 312, 314, 316 formed in the sidewall of the hollow tube 202. The apertures 312, 314, 316 are evenly spaced in a longitudinal direction of the hollow tube 202. Together, the three apertures span a length Z, which is similar to the length Z for window 210 of guide tube 200. The window 310 is arranged such that, when the electrode lead 100 is received in the longitudinal channel of the hollow tube 202, portions of the proximal electrode 104 are exposed via the apertures 312, 314, 316. Thus, the window 310 fulfils a similar function to the window 210 of guide tube 200.

The inventors have found that by forming the window 310 as a series of smaller apertures, it may be possible to increase a rigidity of the hollow tube 202, which may facilitate insertion of the hollow tube 202 into the patient's brain. In the example shown, the window 310 includes three apertures. However, in other examples, different numbers of apertures may be used, e.g. two, four, five or six apertures, and the size and/or spacing of the apertures may be different to that discussed above.

FIG. 3b is a schematic diagram showing an apparatus according to an embodiment of the invention, the apparatus including guide tube 300 and electrode lead 100. FIG. 3b illustrates a configuration where the electrode lead 100 is received in the longitudinal channel in the hollow tube 202 of the guide tube 300. As can be seen in FIG. 3b, in this configuration, the distal portion of the electrode lead 100 comprising the plurality of electrodes 102 protrudes from the distal opening 208 of the hollow tube 202. Moreover, a portion of the proximal electrode 104 is exposed via the apertures 312, 314, 316 of window 310. A proximal end of the electrode lead 100 extends through the inlet in the cap 204 of the guide tube 200, and is connected to a controller 318 in the form of an IPG. The controller is configured to generate neuromodulation signals applied by the proximal electrode 104 and the plurality of electrodes 102.

Figure 4A:
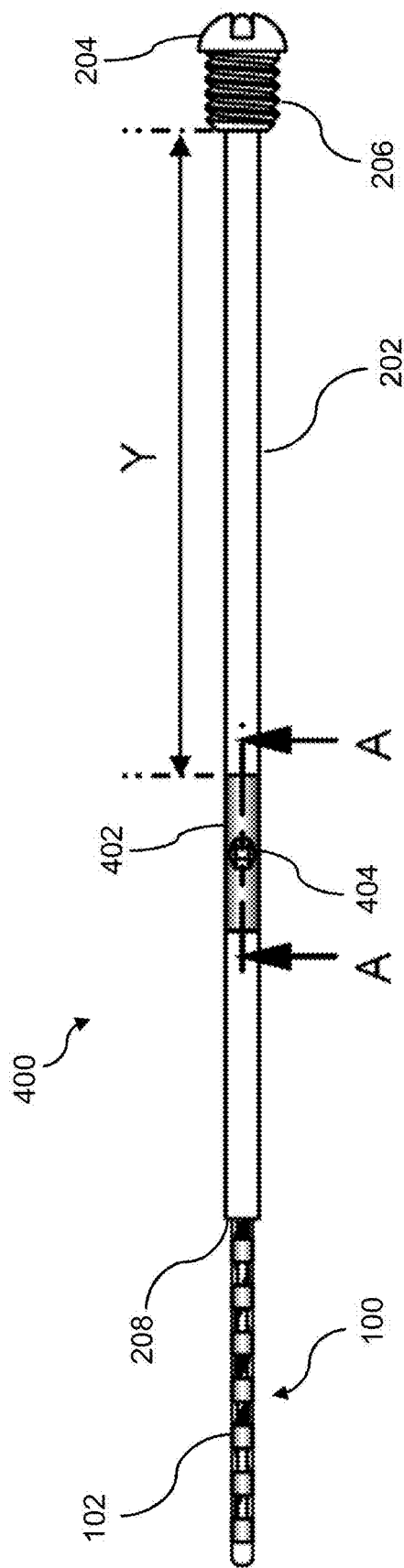
FIG. 4a is a schematic diagram of a guide tube according to an embodiment of the invention.

FIG. 4a shows a schematic diagram of a guide tube 400 according to another embodiment of the invention. The guide tube 400 may form part of an apparatus according to an embodiment of the invention. The guide tube 400 is similar to guide tube 200 described above, however it does not include a window. Accordingly, features of guide tube 400 corresponding to those described in relation to guide tube 200 are indicated in FIG. 4a with the same reference numerals as in FIG. 2a, and are not described again. In the example shown in FIG. 4a, electrode lead 100 is received in the hollow channel in the hollow tube 202 of guide tube 400.

Figure 4B:
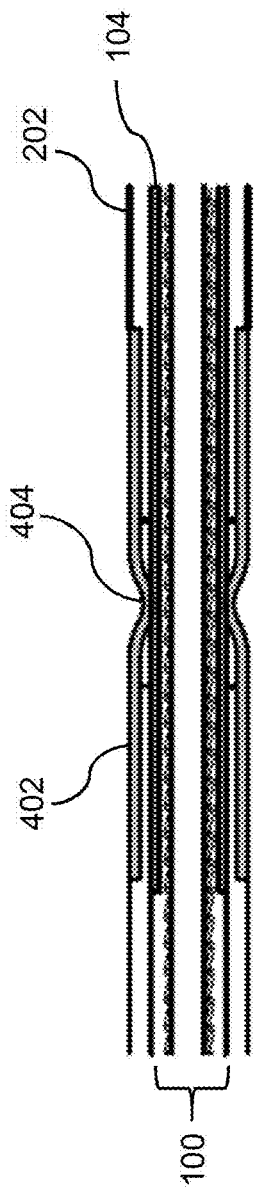

The guide tube 400 includes an outer electrode 402 exposed on an outer surface of the hollow tube 202 of the guide tube 400. The outer electrode 402 has a generally cylindrical shape, and forms part of a sidewall of the hollow tube 202. The outer electrode 402 is made of a conductive material, e.g. platinum-iridium. The outer electrode 402 is configured for electrical connection to a proximal electrode on an electrode lead, e.g. proximal electrode 104 on the electrode lead 100, when the electrode lead is received in the longitudinal channel of the hollow tube 202. FIG. 4b shows an expanded cross-sectional view of the hollow tube 202 along section A-A shown in FIG. 4a, where the electrode lead 100 is received in the longitudinal channel of the hollow tube 202.

The outer electrode 402 includes a depression 404 formed therein, and arranged to contact the proximal electrode 104 when the electrode lead is received in the longitudinal channel of the hollow tube 202. In particular, the depression 404 passes through the sidewall of the hollow tube 202, in order to contact the proximal electrode 104 disposed inside the hollow tube 202. The depression 404 is arranged to form a sliding contact with the proximal electrode 104, to enable insertion of the electrode lead 100 through the longitudinal channel in the hollow tube 202. Thus, when the electrode lead 100 is received in the longitudinal channel of the hollow tube 202, the outer electrode 402 is electrically connected to the proximal electrode 104, via the depression 404 in the outer electrode 402. In this manner, a neuromodulation signal applied to the proximal electrode 104 may be transmitted to the outer electrode 402, which may in turn apply the neuromodulation signal to surrounding target tissue.

Depression 404 may alternatively be referred to as a protrusion that protrudes into the hollow tube 202 to contact the proximal electrode 104.

Mechanisms other than the depression 404 may be used to electrically connect the outer electrode 402 to the proximal electrode 104. For example, instead of the depression 404, a connector may be provided which extends through the sidewall of the hollow tube, between the outer electrode 402 and the longitudinal channel in the hollow tube 202.

The outer electrode 402 is positioned to enable neurostimulation of the DACC and/or CC. The outer electrode 402 may thus provide an alternative to the windows 210 and 310 discussed above, in order to apply a neuromodulation signal to the DACC and/or CC via the proximal electrode 104. For example, the distance Y (shown in FIG. 4a) between the cap 204 and the outer electrode 402 may correspond to a distance between the subject's skull and the DACC. Guide tubes have different distances Y may be provided to accommodate for variations in anatomy between subjects.

The hollow tube 202 of the guide tube 400 may typically be made of a plastic material such as polycarbonate urethane. One method of forming the hollow tube 202 of the guide tube 400 involves forming two thin-walled (e.g. 0.2 mm) concentric extruded tubes of an appropriate diameter. A window may then be formed in the inner tube for receiving the depression 404 (or connector). The outer electrode 402 and outer tube may then be mounted over the inner tube, and the plastic forming the tubes may be reflowed at high temperature on a mandrel to form a bond between the inner and outer tube and contact without introduction of adhesives.

Figure 5:
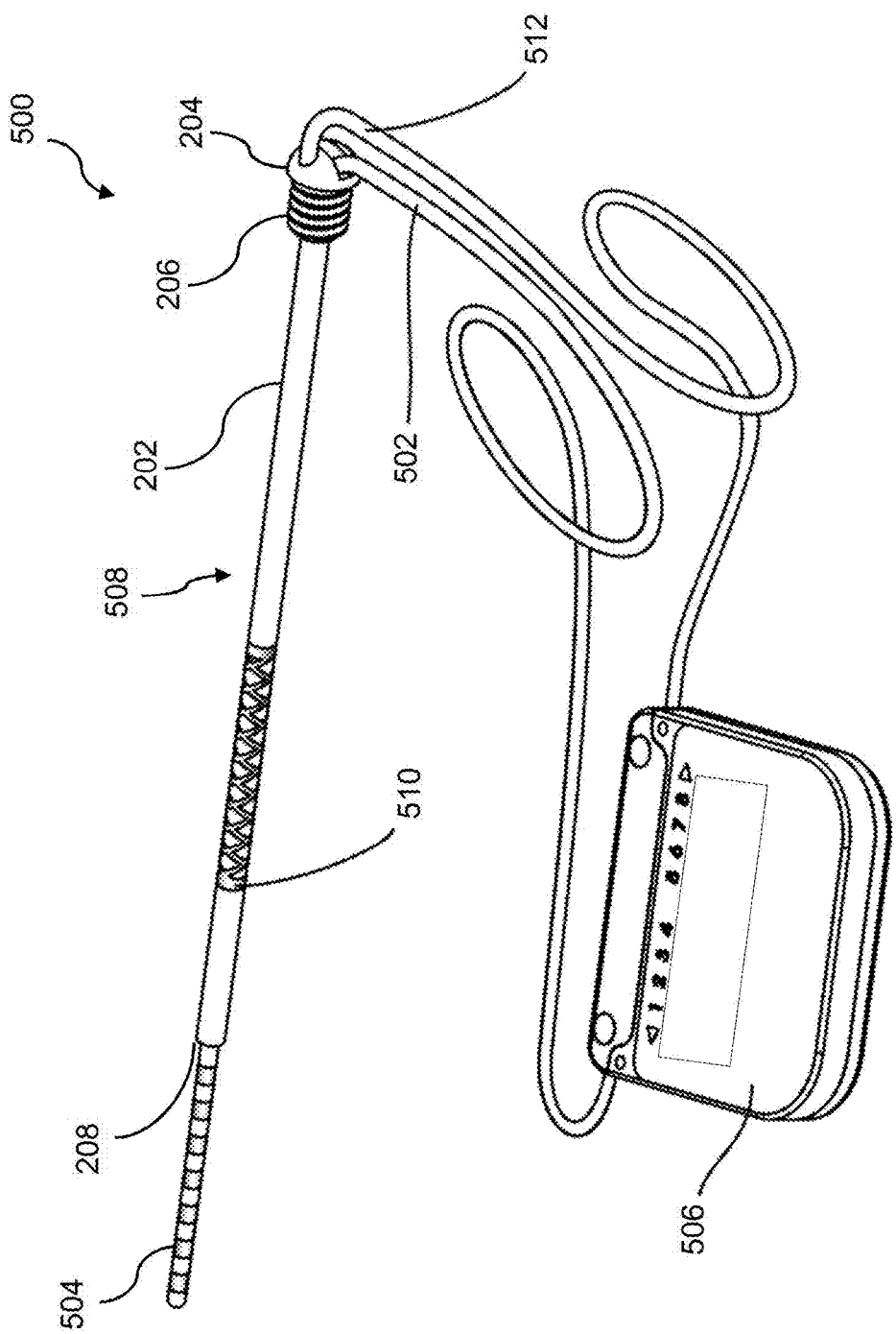
FIG. 5 is a schematic diagram of an apparatus according to an embodiment of the invention.

FIG. 5 illustrates an apparatus 500 according to an embodiment of the invention. The apparatus includes an electrode lead 502, which has a similar configuration to the electrode lead 100 described above. In particular, the electrode lead includes a plurality of electrodes 504 on a distal portion of the electrode lead 504. However, unlike electrode lead 100, electrode lead 502 does not have a proximal electrode. A proximal end of the electrode lead 502 is connected to a controller 506, which is configured to generate neuromodulation signals applied by the plurality of electrodes 504.

The apparatus 500 further includes a guide tube 508. The guide tube 508 is similar to guide tube 200 described above, however it does not include a window. Accordingly, features of guide tube 508 corresponding to those described in relation to guide tube 200 are indicated in FIG. 5 with the same reference numerals as in FIG. 2a, and are not described again.

In the example shown in FIG. 5, the electrode lead 502 is received in the hollow channel in the hollow tube 202 of guide tube 508. The proximal end of the electrode lead 502 protrudes from the inlet in the cap 204 of the guide tube 508, so that it may be connected to the controller 506. The distal portion of the electrode lead 504 protrudes from the distal opening 208 of the hollow tube 202, so that the plurality of electrodes 504 is exposed.

The guide tube 508 includes an outer electrode in the form of a mesh electrode 510 disposed on an outer surface of the hollow tube 202. The mesh electrode 510 is formed of a metallic mesh material which is secured to, or otherwise incorporated into, the outer surface of the hollow tube 202.

The mesh electrode 510 is electrically connected to the controller 506 via a connecting lead 512 which extends from the cap 204 of the guide tube 508. Inside the hollow tube 202, the connecting lead 512 is in the form of a fine connecting wire which extends between the cap 204 and the mesh electrode 510. The fine connecting wire may either be disposed within the longitudinal channel in the hollow tube 202, or it may be embedded in a material forming the hollow tube 202. In this manner, a neuromodulation signal generated by the controller 506 may be conveyed to the mesh electrode 510, which may in turn apply the neuromodulation signal to surrounding brain tissue.

The mesh electrode 510 is positioned to apply a neuromodulation signal to the DACC and/or CC. For example, a distance between the cap 204 and the mesh electrode 508 may correspond to a distance between the skull and DACC. In this manner, a neuromodulation signal may be applied to the DACC and/or CC via the mesh electrode, without having to include a proximal electrode on the electrode lead 504.

Of course, in other embodiments a different form of electrode may be used instead of the mesh electrode 510. For example, a cylindrical electrode may be used instead of the mesh electrode 510.

Figure 6A:
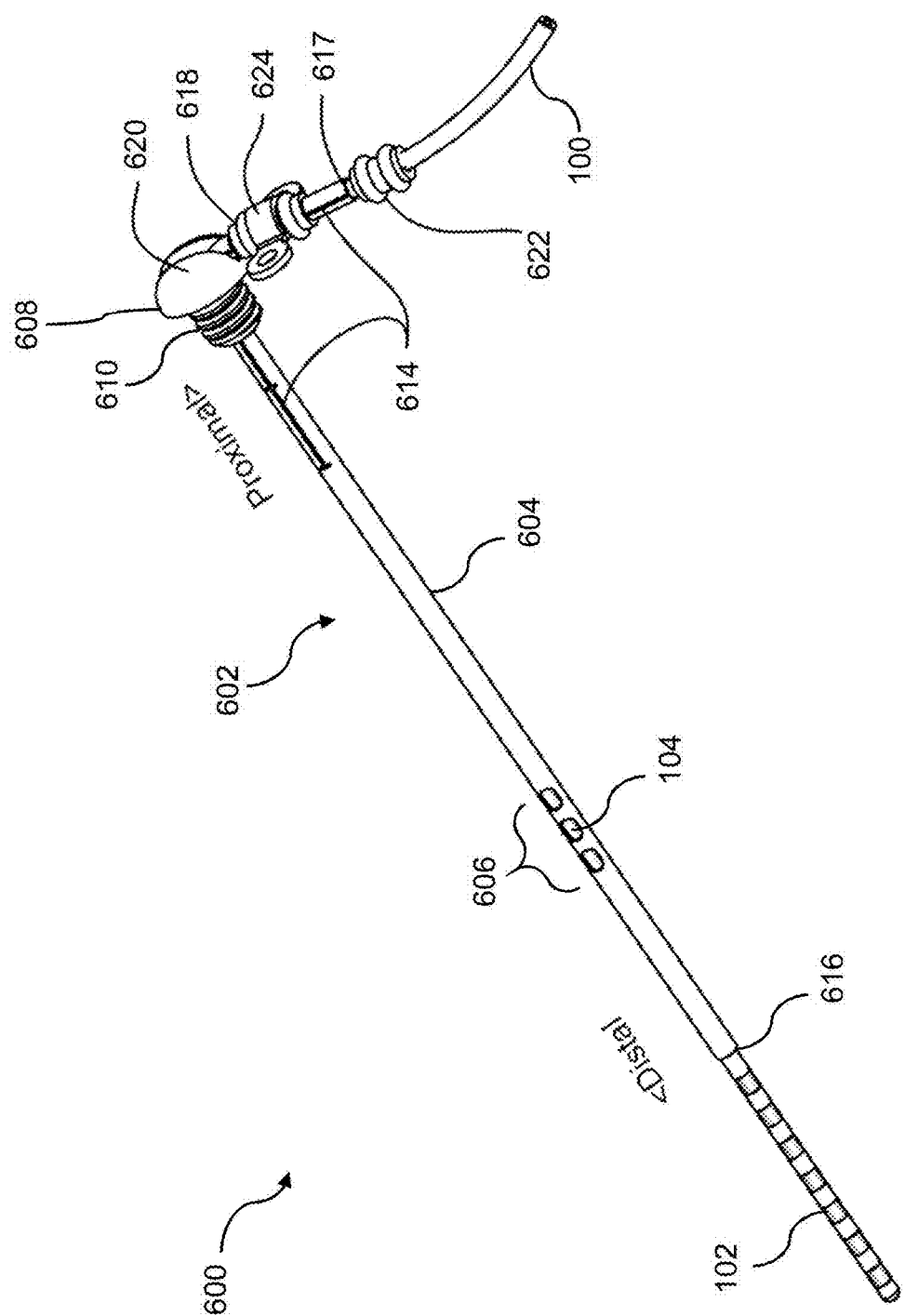
FIG. 6a is a schematic diagram of an apparatus according to an embodiment of the invention.
Figure 6B:
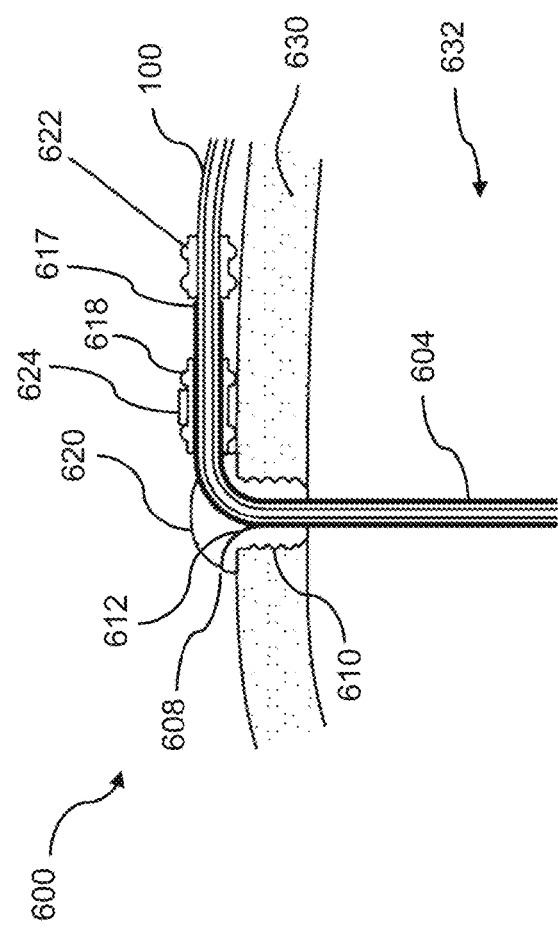
Figure 6C:
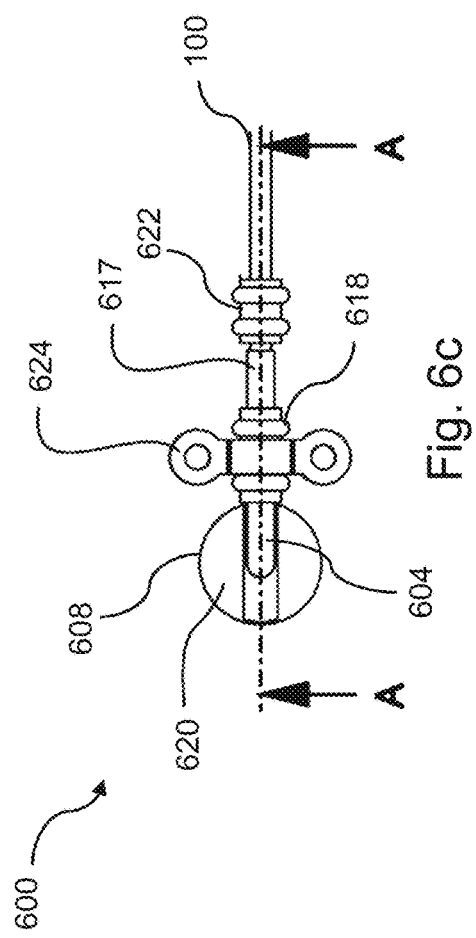

FIGS. 6a, 6b and 6c illustrate an apparatus 600 according to an embodiment of the invention. The apparatus 600 includes electrode lead 100 described above. A proximal end of the electrode lead 100 may be connected to a controller (not shown) for generating neuromodulation signals applied by the plurality of electrodes 102 and the proximal electrode 104. The apparatus 600 further includes a guide tube 602. The guide tube 602 includes a hollow tube 604 defining a longitudinal channel in which the electrode lead 100 is receivable. The hollow tube 604 includes a window 606 in the form of three apertures in a sidewall of the hollow tube 604. The window 606 serves to expose the proximal electrode 104 of the electrode lead 100 to an outside of the hollow tube 604, when the electrode lead 100 is received in the hollow tube 604.

The guide tube 602 further includes a cap 608. The cap 608 is securable in a hole in the subject's skull, via a threaded outer surface 610 on the cap 608. The cap 608 includes a passageway 612 (see FIG. 6b) through which the hollow tube 604 is insertable to insert the hollow tube 604 into the subject's brain. Thus, when the cap 608 is secured in a hole in the subject's hole, the hollow tube 604 may be inserted into the subject's brain via the passageway 612 in the cap 608. The cap 608 is separate from the hollow tube 604, i.e. the cap 608 is not fixed relative to the hollow tube 604, such that a position of the hollow tube 604 relative to the cap 608 may be adjusted. The passageway 612 in the cap may be arranged to form a sliding seal around the hollow tube 604, to prevent leakages through the cap 608.

The hollow tube 604 includes a graduated line 614 which indicates an orientation of the window 606, i.e. a direction in which the window 606 is facing. The graduated line 614 also includes distance markers for indicating a distance between the cap 608 and the window 606 when the hollow tube 604 is inserted through the passageway 612 in the cap 608. In this manner, a user may ensure that the window 606 is inserted at a correct depth and orientation into the subject's brain.

The hollow tube 604 may be supplied straight, to facilitate insertion of the hollow tube through the passageway 612 in the cap. Prior to insertion, a distal end 616 of the hollow tube 604 may be cut to an appropriate length, e.g. so that when inserted the distal end 616 of the hollow tube 604 may extend a few millimetres below the lateral ventricle.

The guide tube 602 includes a first limiter 618 which is secured near a proximal end 617 of the hollow tube 604, the first limiter 618 being arranged to abut against a dome 620 of the cap when a pre-determined length of the hollow tube 604 is inserted through the passageway.

The first limiter 618 may be positioned on the proximal portion of the hollow tube 604 such that, when the first limiter 618 abuts against the dome 620 of the cap 608, the window 606 and distal end 616 of the hollow tube 604 are at a required depth. In particular, the pre-determined length may be arranged such that the window 606 is adjacent to the DACC (so that a neuromodulation signal can be applied to the DACC and/or CC via the proximal electrode), and such that the distal end 616 of the hollow tube is a few millimetres below the lateral ventricle. The ability to adjust the position of the hollow tube 604 relative to the cap 608 may enable the guide tube 602 to be adapted to the specific anatomy of the subject.

The position of the first limiter 618 on the proximal portion of the hollow tube 604 may be set, e.g. based on markings on the graduated line 614.

The first limiter 618 may be secured to the hollow tube 604 using any suitable means, e.g. with sutures, adhesive, or a clamping mechanism.

The proximal end 617 of the hollow tube 604 may be cut to ensure sufficient length for securing the first limiter 618 to the hollow tube 604.

In practice, the hollow tube 604 may be introduced into the subject's brain via the passageway 612 in the cap 608 over a straight guide rod which is aligned along a desired trajectory, e.g. using a stereotactic frame or stereotactic robot. Once the hollow tube is inserted to the correct depth, i.e. when the first limiter 618 abuts against the dome 620 of the cap 608, the guide rod may be withdrawn. The electrode lead 100 may then be inserted into the subject's brain via the longitudinal passageway in the hollow tube 604, and into a tract formed in the subject's brain by the guide rod.

A second limiter 622 is secured to a proximal portion of the electrode lead 100. The second limiter 622 is positioned on the electrode lead 100 such that the second limiter 622 abuts against the proximal end 617 of the hollow tube 604 when a pre-determined length of the electrode lead 100 protrudes through an opening at the distal end 616 of the hollow tube 604.

In this manner, it is possible to ensure that the distal portion of the electrode lead comprising the plurality of electrodes 102 is inserted into the subject's brain to an appropriate depth. This may also serve to ensure that the proximal electrode 104 on the electrode lead 100 is properly aligned with the window 606. The second limiter 622 may be secured to the electrode lead 100 using any suitable means, e.g. with sutures, adhesive, or a clamping mechanism.

Following insertion of the electrode lead 100 into the hollow tube 604, a proximal portion of the hollow tube 604 and the electrode lead 100 protruding from the cap 608 may be bent through an angle of approximately 90 degrees. The first limiter 618 is then secured to the subject's skull via a fixation 624 (e.g. miniplate) which may be screwed to the subject's skull using bone screws (not shown). Such a configuration is illustrated in FIGS. 6a, 6b and 6c.

The hollow tube 604 may be made of a thermoplastic material, to facilitate bending the hollow tube 604 through the approximately 90 degree angle, e.g. the thermoplastic material may be heated to enable the hollow tube 604 to bend, and it may then harden upon cooling.

The first limiter 618 includes a groove formed in an outer surface thereof for receiving the fixation 624. Engagement between the groove and the fixation 624 may ensure that the first limiter 618 is securely held in place by the fixation 624. As the first limiter 618 is secured to the hollow tube 604, the fixation 624 may prevent the hollow tube 604 from moving relative to the skull.

FIG. 6b shows a cross-sectional view of apparatus 600 along section A-A depicted in FIG. 6c. The apparatus 600 is mounted on a subject's skull 630. The cap 608 is secured in a hole formed in the subject's skull 630, with the hollow tube 604 being inserted into the subject's brain 632 via the passageway 612 in the cap 608. The hollow tube 604 is secured to the subject's skull 630 via the fixation 624 which is engaged in the groove of the first limiter 618, the fixation 624 being screwed to the subject's skull 630. FIG. 6c shows a top view of apparatus 600 mounted on the subject's skull 630.

FIGS. 7a and 7b illustrate an apparatus 701 according to an embodiment of the invention, the apparatus 701 including a guide tube 700 (which is also an embodiment of the invention). The guide tube 700 is similar to guide tube 602 described above, however it does not include a window for exposing a proximal electrode. Accordingly, features of guide tube 700 corresponding to those described in relation to guide tube 604 are indicated in FIGS. 7a and 7b with the same reference numerals as in FIGS. 6a, 6b and 6c, and are not described again. The apparatus 701 further includes an electrode lead 702.

FIG. 7a shows a cross-sectional view of a portion of the hollow tube 604 of the guide tube 700. In the example shown, the electrode lead 702 is received in the longitudinal channel in the hollow tube 604. The electrode lead 702 has a similar configuration to the electrode lead 100 described above; in particular, the electrode lead 702 includes a distal portion having a plurality of electrodes 704 thereon, and a proximal electrode 706 spaced apart from the plurality of electrodes 704.

The hollow tube 604 of guide tube 700 includes a cylindrical conductor 708 embedded within a plastic material forming the hollow tube 604. An inner surface of the cylindrical conductor 708 forms a section of the longitudinal channel in the hollow tube 604. In this manner, when the electrode lead 702 is received in the longitudinal channel in the hollow tube 604, the proximal electrode 706 may come into contact with the cylindrical conductor 708, as shown in FIG. 7a.

A window 710 is formed in the plastic material of the hollow tube 604, which exposes a portion of the cylindrical conductor 708. The exposed portion of the cylindrical conductor 708 thus constitutes an outer electrode which is exposed at an outer surface of the hollow tube 604. In this manner, a neuromodulation signal applied to the proximal electrode 706 of the electrode lead 702 may be transmitted to the cylindrical conductor 708, which may in turn apply the neuromodulation signal to target tissue via the window 710. The window 710 may be dimensioned to apply enable directional neurostimulation of the DACC and/or CC. As the proximal electrode 706 of the electrode lead 702 is not used for directly apply a neuromodulation signal to the DACC, it may be possible to reduce a length of the proximal electrode 706.

Similarly to guide tube 602, the hollow tube 604 of guide tube 700 is insertable through a passageway in the cap 608, so that a length of the hollow tube 604 inserted into the subject's brain may be adjusted. The first limiter 618 on the proximal portion of the hollow tube 604 may be positioned and secured to ensure that the window 710 is positioned at a desired depth in the subject's brain. The hollow tube 604 of guide tube 700 includes a graduated line 712 which indicates an orientation of the window 710, i.e. a direction in which the window 606 is facing. The graduated line 712 also includes distance markers for indicating a distance between the cap 608 and the window 710 when the hollow tube 604 is inserted through the passageway in the cap 608.

In the example shown in FIG. 7b, the hollow tube 604 and electrode lead 702 are in a straight configuration, i.e. prior to bending of the hollow tube 604 and electrode lead 702 and attachment of the first limiter to the subject's skull (discussed above in relation to FIGS. 6a, 6b and 6c). As can be seen in FIG. 7b, the electrode lead 702 includes a second limiter 714 secured to a proximal end thereof, to ensure that a desired length of the electrode lead protrudes from the opening at the distal end 616 of the hollow tube 604.

In practice, relative positions of the distal end 616 of the hollow tube, the window 710 and the cap 608 may be determined by choosing appropriate values for dimensions X and Y illustrated in FIG. 7b. Dimension X, which corresponds to a distance between the distal end 616 of the hollow tube 604 and the window 710 may be adjusted by cutting the distal end 616 of the hollow tube 604. Dimension Y, which corresponds to a distance between the cap 608 and the window 710, may be adjusted by sliding the cap 608 relative to the hollow tube 604. A proximal portion of the hollow tube 604 which protrudes from the cap 608 may be cut to an appropriate length (shown as Z in FIG. 7b) for accommodating the first limiter 618. Similar principles may be applied for adjusting various dimensions of guide tube 602 described above.

Figure 8:
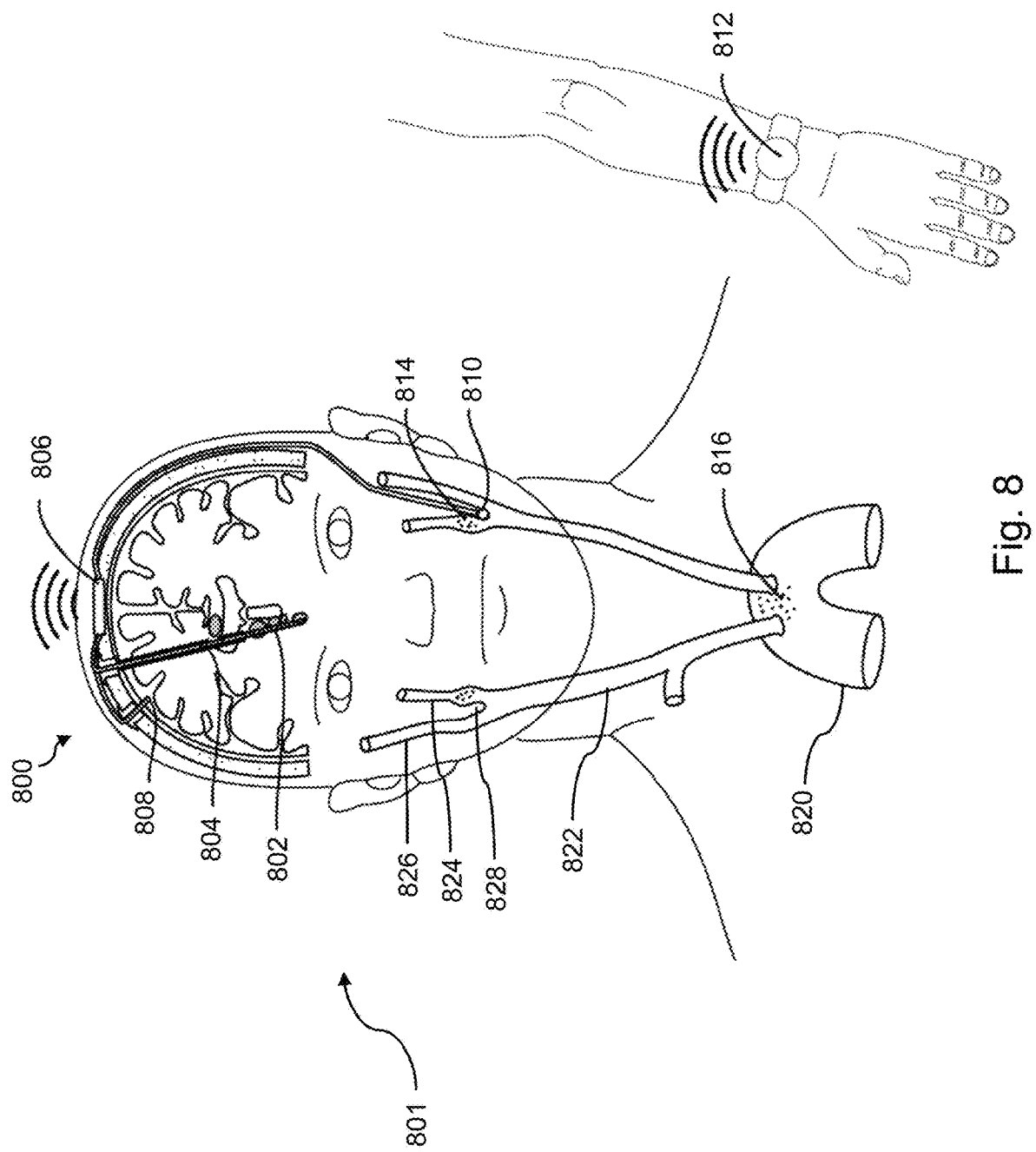
FIG. 8 is a schematic diagram showing an apparatus according to an embodiment of the invention in use on a subject.

FIG. 8 is a schematic diagram illustrating an apparatus 800 according to an embodiment of the invention. In the example shown, the apparatus is in use on a subject 801. The apparatus includes an electrode lead 802 which is implanted into the subject's brain via a guide tube 804. The electrode lead 802 may correspond, for example, to electrode lead 100 described above, whilst the guide tube 804 may correspond to guide tube 200 or 300 described above. Any of the electrode leads and guide tubes discussed above may be used as part of apparatus 800. The guide tube 804 is inserted into the subject's brain via a burr hole in the subject's skull, with the cap of the guide tube 804 being secured to the subject's skull. The electrode lead 802 is implanted into the subject's brain along a linear trajectory which passes adjacent to the DACC, through the DMN, adjacent to the LH and the PC, and into the VL-PAG. In this manner, a neuromodulation signal may be applied to the DACC and/or CC via the proximal electrode whilst the DMN, LH, PC and VL-PAG may be stimulated via the plurality of electrodes on the electrode lead 802.

The electrode lead 802 is connected to a controller 806 in the form of an IPG. The controller 806 is implanted into a pocket formed in the subject's skull. The controller 806 is configured to generate neuromodulation signals applied by the electrodes on the electrode lead 802.

The apparatus 800 includes multiple sensors which are communicatively coupled to the controller, and which are arranged to detect various physiological parameters of the subject 801. The apparatus 800 includes an intracranial pressure (ICP) sensor 808 which is arranged to detect an ICP of the subject 801. In the example shown, the ICP sensor 808 is implanted under the subject's skull via a second burr hole in the subject's skull. The ICP sensor 808 is communicatively coupled to the controller 806 via a wire, so that the ICP sensor 808 can transmit a signal relating to the subject's ICP to the controller 806. Additionally or alternatively, an ICP sensor may be incorporated into the guide tube 804 and/or the electrode lead 802. Incorporating the ICP sensor into the guide tube 804 and/or the electrode lead 802 may avoid having to make a second burr hole in the subject's skull.

The apparatus 800 further includes an internal sensor 810 for detecting blood flow and/or blood pressure. In the example shown, the internal sensor 810 is implanted over the carotid bifurcation. The internal sensor 810 is communicatively coupled to the controller 806 via a wire, so that the internal sensor 810 can transmit a signal relating to the subject's blood flow and/or blood pressure to the controller 806. The apparatus may also include a wearable sensor, e.g. in the form a wrist-mountable sensor 812. The wrist-mountable sensor 812 may, for example, be configured to detect blood pressure, heart rate, or blood flow. The wrist-mountable sensor 812 may be communicatively coupled to the controller via a wireless connection between the controller 806 and the sensor 812, so that the sensor 812 can transmit a signal relating to the measured physiological parameter(s) to the controller 806. Different embodiments may include different types of sensors arranged to detect different physiological parameters of the subject, and communicate signals relating to the detected physiological parameters to the controller 806.

The controller 806 is configured to adjust one or more of the neuromodulation signals applied via the electrode lead 802 based on the physiological parameters detected by the sensors (e.g. ICP sensor 808 and/or wrist-mountable sensor 812). In this manner, control of the neuromodulation signals may be based on feedback provided by the subject's physiological parameters. The controller 806 may be configured to adjust one or more of the neuromodulation signals applied via the electrode lead 802, in order to reach a set point associated with one of the physiological parameters.

The controller 806 may further be configured to detect a circadian rhythm of the subject 801. This may be done by monitoring physiological parameters of the subject such as blood pressure and/or heart rate, which vary diurnally in accordance with the subject's circadian rhythm. Similarly, the controller 806 may be configured to detect a disturbance in the subject's circadian rhythm, e.g. by comparing diurnal variations in the measured physiological parameters with model diurnal variations corresponding to a non-disturbed circadian rhythm. The controller 806 may then adjust the one or more neuromodulation signals based on the circadian rhythm, and/or to re-establish a normal circadian rhythm in the subject 801.

FIG. 8 shows the location of carotid baroreceptors and the carotid bodies. The ascending aorta 820 feeds the carotid artery 822. Bifurcation of the internal carotid 824 and the external carotid 826 forms a saddle in which the carotid body 828 is located. Aortic arch baroreceptors 816 feed the vagus nerve which is routed to the medulla. Carotid baroreceptors are located on the internal carotid artery 824 and in the carotid sinus 814. Both the carotid bodies and carotid baroreceptors feed the sinus nerve of Herring which joins the glossopharyngeal nerve before reaching the medulla.

In some embodiments, the apparatus 800 may further include one or more stimulation electrodes for applying one or more simulation signals to a carotid body and/or a carotid baroreceptor in the subject 801. For example, the internal sensor 810 may include a stimulation electrode arranged to apply a stimulation signal to baroreceptors in the carotid sinus 814 and/or to the carotid body 828. Alternatively, a separate stimulation electrode may be provided for applying a stimulation signal to baroreceptors in the carotid sinus 814. A separate stimulation electrode may also be provided for applying a stimulation signal to baroreceptors in the aortic arch 816.

The one or more stimulation electrodes may form part of an implantable lead which is implanted into the subject. The implantable lead may be similar to one described in US 2015/0112359 A1. For example, the implantable lead may include a semi-circular hook which enables the implantable lead to sit over the bifurcation of the internal carotid 824 and the external carotid 826. The semi-circular hook may include a stimulation electrode arranged such that the stimulation electrode is held in close proximity to the carotid body and/or to carotid baroreceptors in the carotid sinus. The implantable lead may be implanted into the subject 801 using a guide tube or needle.

The stimulation signals applied by the one or more stimulation electrodes may be generated by the controller 806, in which case a wired connection may be provided between the controller 806 and the stimulation electrodes. Alternatively, a separate controller (not shown) may be provided to generate the stimulation signals applied by the one or more stimulation electrodes.

The stimulation signals applied by the one or more stimulation electrodes may be in the form of pulsed RF electrical signals. A pulse duration of the stimulation signal may be 2 to 10 ms or preferably 5 to 8 ms, each pulse consisting of many cycles of a RF waveform of 200 to 600 kHz, or preferably 250 to 500 kHz. The pulses may be repeated at 2 to 8 Hz, preferably at 5 Hz, with a space between each pulse approximately 120 to 500 ms. Typically, an amplitude of the pulsed RF signal may be 25 to 100 V or 10 V to 140 V is employed. Such pulsed RF signals may avoid build-up of heat generated at the one or more stimulation electrodes, in order to avoid tissue ablation which may cause long term damage to nerves or carotid bodies. Such stimulation signals may be applied intermittently to the carotid body.

Alternatively, the stimulation signals applied to the carotid baroreceptor may have pulsed amplitude typically between 5 to 10 mA, pulsed width typically between 45 to 210 ms, and pulsed frequency typically between 40 and 80 Hz. Such stimulation signals have been demonstrated to produce blood pressure response. Such stimulation signals may be applied continuously to the carotid baroreceptor, for example with appropriate cycling or bursting.

FIG. 9 is a schematic diagram illustrating an apparatus 900 according to an embodiment of the invention. In the example shown, the apparatus 900 is mounted on a subject's skull 901. The apparatus 900 includes a controller 902 in the form of an IPG which is implanted into a pocket formed in the subject's skull 901. The controller 902 is electrically connected to an electrode lead 904, which is implanted via a hole in the subject's skull 901 into the subject's brain. The electrode lead may, for example, be similar in configuration to electrode lead 100 described above. The electrode lead 904 is secured to the subject's skull via a fixation (e.g. miniplate) 906.

The controller 902 is powered by an external power supply which includes a transmitter coil 908 which is arranged to sit on the subject's scalp. The transmitter coil 908 is configured to transmit power to the controller 902 via inductive coupling between the transmitter coil 908 and the controller (e.g. a receiver coil in the controller). In this manner, power may be wirelessly transmitted from the external power supply to the controller 902. This may avoid having to include an internal power supply in the controller 906, and facilitate coupling of the controller 902 to an external power supply. The external power supply may, for example, be configured to deliver power continuously, or in bursts at programmed times. The apparatus 900 may further include a cap (not shown) which is arranged to hold the transmitter coil 908 in place over the controller 906.

Figure 10B:
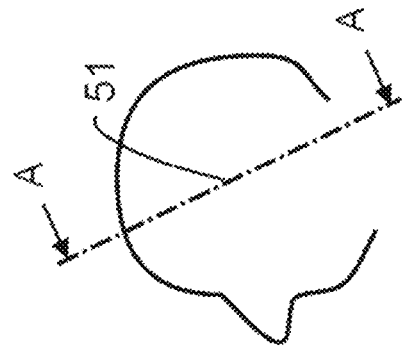
Figure 10A:
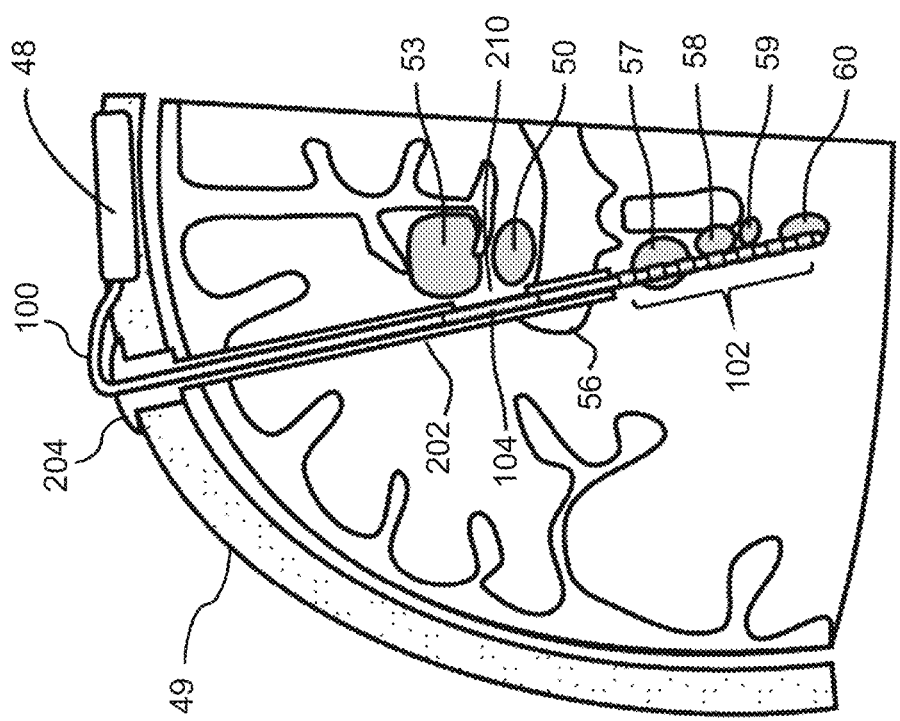
FIG. 10a is a cross-sectional view of a subject's head showing an apparatus according to an embodiment of the invention in use on the subject.

FIGS. 10a and 10b illustrate placement of an electrode lead in a subject's brain along a preferred trajectory, to enable a treatment according to an embodiment of the invention.

In the example shown in FIG. 10a, electrode lead 100 is implanted into the subject's brain via guide tube 200, described above. However, other electrode leads and guide tubes described herein may be implanted along the trajectory shown in FIG. 10a. FIG. 10b shows a side view of a subject's head, and depicts a cross-sectional line 51 (A-A). FIG. 10a shows a cross-sectional view of the subject's head along cross-sectional line 51.

The cap 204 of the guide tube 200 is secured to a hole in the subject's skull 49. The hollow tube 202 of the guide tube 200 is implanted into the subject's brain along a straight-line trajectory which passes lateral to the DACC 53 and the corpus callosum 50, and which further passes through the DMN 57, adjacent to the LH 58 and PC 59, into the VL-PAG 60. The hollow tube 202 traverses the lateral ventricle 56, the distal opening 208 of the hollow tube 202 being located a few millimetres below the lateral ventricle 56. The electrode lead 100 is implanted into the subject's brain via the guide tube 200 along the straight-line trajectory.

The distal portion of the electrode lead comprising the plurality of electrodes 102 protrudes from the distal opening 208 of the guide tube, such that it passes through the DMN 57, adjacent to the LH 58 and PC 59, and into the VL-PAG 60.

The window 210 in the hollow tube 210 is disposed adjacent to the DACC 53 and the corpus callosum 50. A portion of the proximal electrode 104 on the electrode lead 100 is exposed via the window 210 in the hollow tube. In this manner, a neuromodulation signal may be applied to the DACC 53 and CC 50 via the proximal electrode 104. Furthermore, the plurality of electrodes 102 on the distal portion of the electrode lead 100 may be used to apply neuromodulation signals to one or more of the DMN 57, the LH 58, the PC 59 and the VL-PAG 60. A controller 48 in the form of an IPG is implanted in a pocket formed in the subject's skull 49. The controller 48 is configured to generate the neuromodulation signals applied by the plurality of electrodes 102 and the proximal electrode 104.

Figure 11:
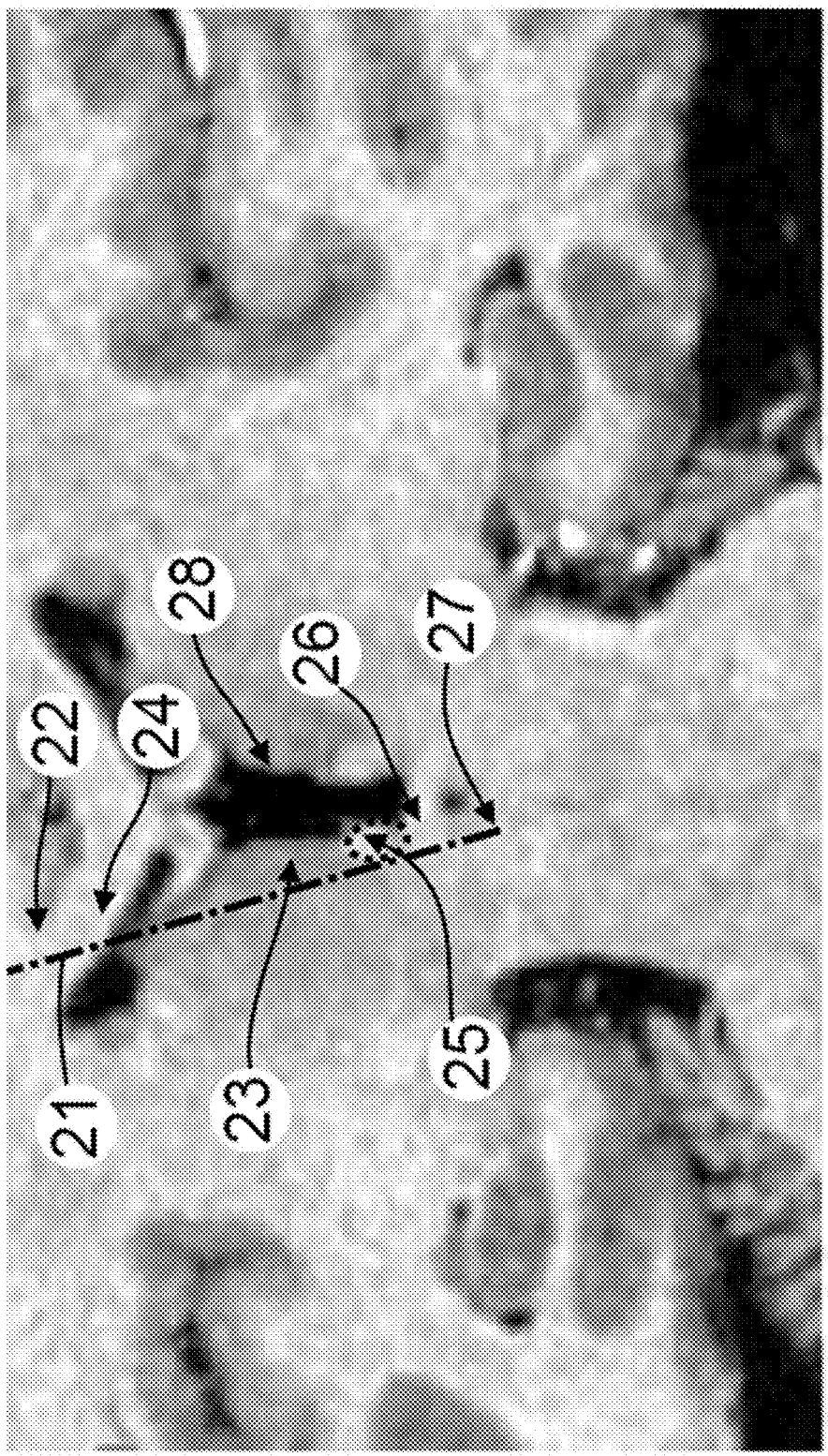
FIG. 11 is an image of a subject's brain showing a trajectory for implanting an electrode lead into the subject's brain according to an embodiment of the invention.

FIG. 11 is a picture of a subject's brain illustrating a preferred trajectory 21 for implanting an electrode lead, according to a method of the invention. The trajectory 21 is a straight-line trajectory that runs lateral to the DACC 22 and the CC 24, traverses the DMN 23, runs adjacent to the LH 25, bypasses the third ventricle 28, runs adjacent to the PC 26, and terminates in the VL-PAG 27. Accordingly, if an electrode lead is implanted into a subject's brain along trajectory 21, one or more of the DACC, CC, DMN, LH, PC and VL-PAG may be stimulated.

Figure 12B:
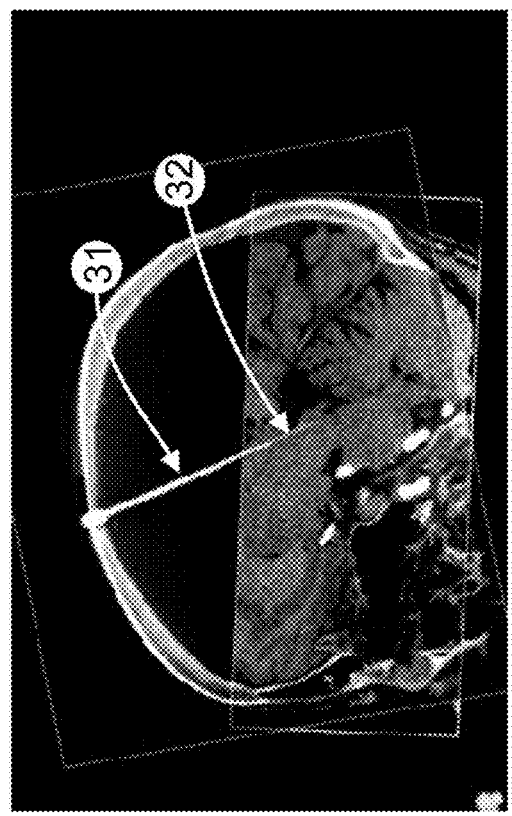
FIGS. 12a and 12b are images of a guide tube implanted into a subject's brain along a preferred trajectory.
Figure 12A:
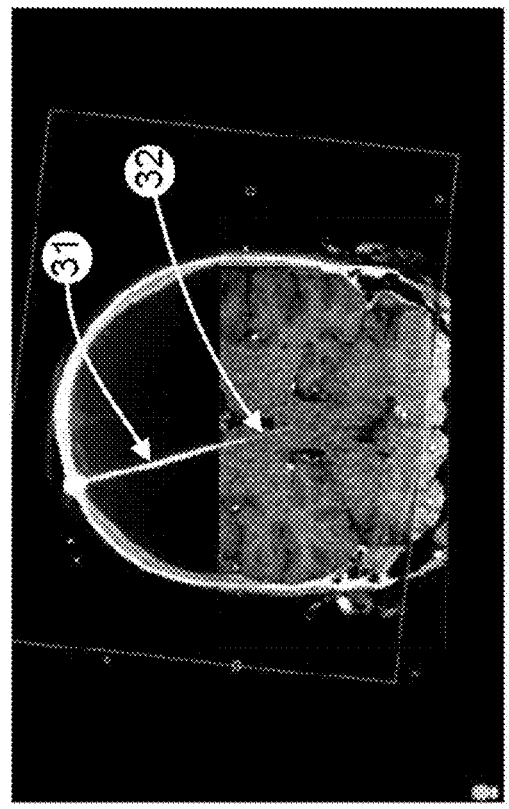

FIGS. 12a and 12b show images of a guide tube 31 implanted into a subject's brain along the trajectory 21 illustrated in FIG. 11, prior to insertion of the electrode lead. FIG. 12a corresponds to an anteroposterior projection of the trajectory 21, whilst FIG. 12b corresponds to a side view of the trajectory 21. A guide rod 32, which is made of a radio opaque material is used to implant the guide tube along the correct trajectory, e.g. using a stereotactic frame or a stereotactic robot.

Figure 13:
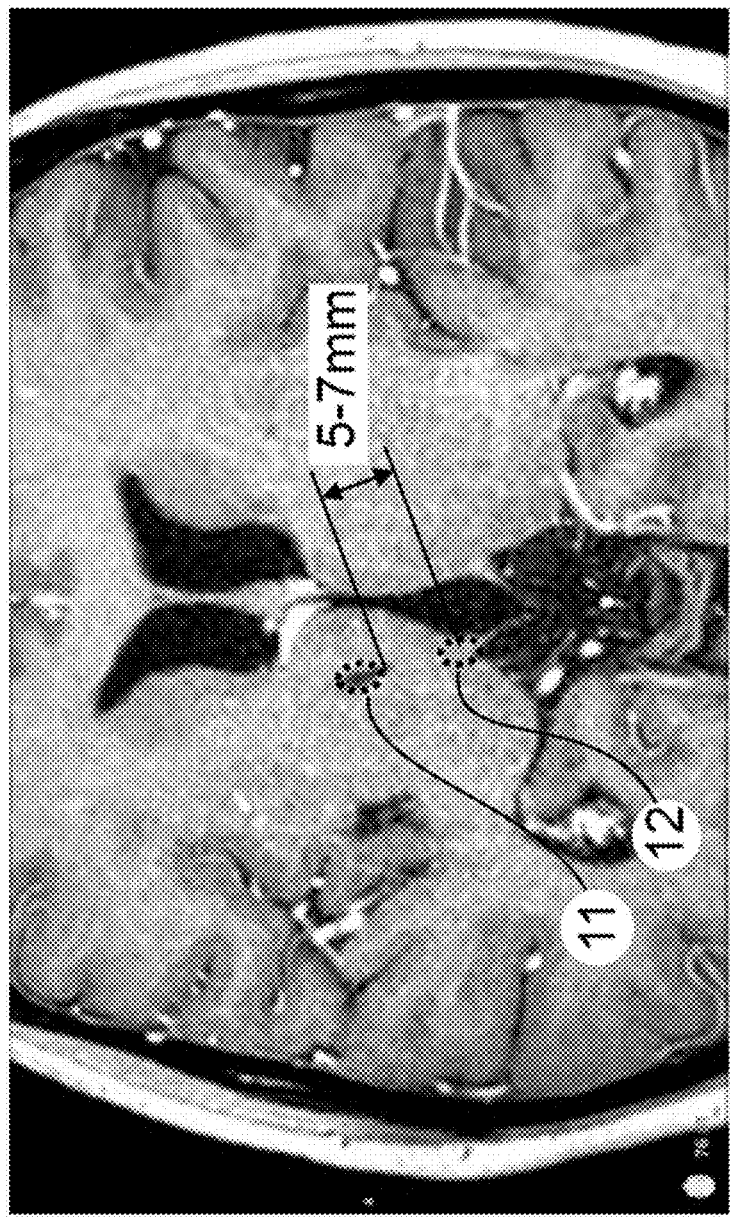
FIG. 13 is an image of a subject's brain showing a deviation of an implanted electrode lead from a preferred trajectory.

FIG. 13 is an image of a subject's brain showing an electrode lead 11 implanted into the subject's brain. The image illustrates a distance between the implanted electrode lead 11 and the LH 12. As shown in FIG. 13, in this case the distance is greater than 5 mm, between 5-7 mm. The inventors found that in cases, such as that illustrated in FIG. 13, where the electrode lead was implanted along a trajectory that passed more than 5 mm anterior to the LH and PC, the subject did not respond to combined stimulation of the DMN and VL-PAG. This was because the electrode lead was too far from the LH and PC, such that the neuromodulation signals could not be effectively applied to the LH and PC.

In one research subject, the electrode lead was as shown in FIG. 13, and the subject did not respond to combined stimulation of the DMN and/or VL-PAG. The inventors found that by revising the trajectory to run closer to the LH and PC (i.e. less than 5 mm away from the LH and PC), they were able to obtain a positive response by combined stimulation of the DMN and VL-PAG together with the LH and PC.

This led to the inventors' realisation that, by applying a neuromodulation signal to the LH and PC, it is possible to enhance a subject's response to neurostimulation of the DMN and/or VL-PAG. It may be preferable for the electrode lead trajectory to pass less than 5 mm from the LH and PC, to ensure that neuromodulation signals may be effectively applied to the LH and PC.

According to the invention, higher frequency neuromodulation signals may be applied to the DMN, whilst lower frequency neuromodulation signals may be applied to the LH and PC. Where a neuromodulation signal is also applied to the VL-PAG, a neuromodulation signal having a lower frequency may also be applied to the VL-PAG.

The higher frequency neuromodulation signal applied to the DMN may, for example, be a train of pulses of forward pulse width 25 to 350 microseconds, more preferably 60 to 90 microseconds, at a repetition frequency of greater than 70 Hz, more preferably in the range 100 to 200 Hz, or 130 or 150 Hz. The forward (negative going) pulses are delivered at amplitude of typically 1 or 2 to 3 or 5 mA with a current controlled output or 1 to 3 V with a voltage controlled output with a balancing reverse charge typically delivered at the same or lower intensity. The higher frequency neuromodulation signal may serve to inhibit neurons in structures such as the dorsomedial nucleus, anterior nucleus and centromedian/parafascicular complex.

The lower neuromodulation signal applied to one or more of the LH, PC and VL-PAG may consist of a train of pulses of forward pulse width 50 to 450 microseconds, at a repetition frequency of 5 or 10 to 40 or 50 Hz, typically 90 to 180 microsecond pulses of 1 or 2 to 3 or 5 mA amplitude with a current controlled output, or 1 to 5 V amplitude with a voltage controlled output. A balancing reverse charge may be required. Preferably the repetition frequency is 5 to 10 Hz or 20 Hz, however in some instances response may be maximised at 40 Hz. Such a lower frequency neuromodulation signal may act to excite neuronal activity in the stimulated targets. The lower frequency neuromodulation signal may serve to excite neurons in structures such as the pineal gland.

Table 1 below summarises a series of tests performed on test subjects, which show the effects of various neurostimulation methods according to embodiments of the invention. Neuromodulation signals were applied to each of the test subjects in order to treat hypertension in the test subjects.

The left-hand column of Table 1 indicates the test subject on which the tests were performed. The column labelled "Stimulation targets" provides an indication of the various targets in the subject's brain to which neuromodulation signals were applied during each test. References to "bilateral", "left" and "right" provide an indication of whether neuromodulation signals were applied to a target in both hemispheres of the brain, or in the left or right hemisphere. The column labelled "Stimulation On/Off" provides an indication of whether measurements were obtained during application of the neuromodulation signals ("On"), or when the neuromodulation signals were signals were switched off ("Off"). The last three columns provide indications of values that were measured during the tests. The column labelled "CBF" provides an indication of the cerebral blood flow. The column labelled "CBV" provides an indication of the cerebral blood volume. The column labelled "MTT" provides an indication of the mean transit time of blood through the brain, i.e. the amount of time spent in the brain, between its times of entering and exiting the brain.

CBV is measured in units of milliliters of blood per 100 g of brain and is defined as the volume of flowing blood for a given volume of brain. MTT is measured in seconds and defined as the average amount of time it takes blood to transit through the given volume of brain. CBF is measured in units of milliliters of blood per 100 g of brain tissue per minute and is defined as the volume of flowing blood moving through a given volume of brain in a specific amount of time.

As can be seen from Table 1, the general effect of applying the neuromodulation signals to targets in the brain is to increase cerebral blood flow and cerebral blood volume. In many cases, mean transit time of blood through the brain is also reduced.

TABLE 1

Summary of test results

| Test subject | Stimulation targets | Stimulation On/Off | CBF | CBV | MTT |
|---|---|---|---|---|---|
| 1 | Bilateral DMN and LH, and left PC and VL-PAG (High amplitudes | On | 19.41 | 1.96 | 8.29 |
|   |   | Off | 17.38 | 1.99 | 9.06 |
| 1 | Left DMN, LH, PC and VL-PAG (High amplitudes) | On | 20.88 | 2.08 | 8.66 |
| 1 | Bilateral DMN, LH (High amplitudes) | On | 22.4 | 1.96 | 7.18 |

TABLE 1-continued

Summary of test results

| Test subject | Stimulation targets | Stimulation On/Off | CBF | CBV | MTT |
|---|---|---|---|---|---|
| 1 | Right DMN, LH and PC | On | 25.5 | 2.0 |  |
|   |   | Off | 16.6 | 1.6 |  |
| 1 | Post-operation, LH and PC | On | 23.6 | 2.04 | 7.3 |
|   |   | Off | 19.9 | 1.71 | 6.8 |
| 1 | Right DMN, LH, PC and VL-PAG | On | 24.7 | 2.1 | 7 |
|   |   | Off | 17.7 | 1.8 | 8 |
| 2 | Right DMN, LH, PC and VL-PAG (Test 1) | On | 27 | 2.5 | 7.3 |
|   |   | Off | 17 | 1.9 | 8.5 |
| 2 | Right DMN, LH, PC and VL-PAG (Test 2) | On | 24 | 2.2 | 7.2 |
|   |   | Off | 18 | 2.3 | 9.9 |
| 3 | Right LH, PC, VL-PAG and bilateral DACC | On | 26.7 | 2.3 | 7.2 |
|   |   | Off (Bilateral DACC remains on) | 24.2 | 1.9 | 6.9 |

Below we provide brief discussions of several conditions that may be treated using a method of the invention.

Hypertension

Hypertension is one of the most important challenges for public health systems. The prevalence of resistant hypertension suggests that existing pharmacological interventions have failed for many patients. This coupled with the fact that some drugs are poorly tolerated by patients, with associated non-adherence, suggests that there is a need for improved medical treatment. The globally accepted diagnosis for treatment resistant hypertension is an office blood pressure measurement exceeding 140/90 millimetres of mercury whilst on pharmacological intervention with three or more anti-hypertensive medications (including a diuretic).

Arterial blood pressure normally shows physiological diurnal fluctuations, with higher levels during the day and lower levels during the night. Hypertensive patients whose pressures remain high at night (non-dippers) have been reported in some studies to show more target organ damage than those who exhibit a normal pattern (dippers). Normally during sleep blood pressure decreases (dips) more than 10% from daytime baseline blood pressure. Additionally in the general population, non-dipping may be a risk factor for cardiovascular disease mortality independent of the overall blood pressure during a 24-hour period, and has been shown to be associated with cardiac hypertrophy and re-modelling.

Non-dipping has been shown to be present in approximately 40% of untreated hypertensives and more than 50% of treated hypertensives. It is possible that non-dipping is an early change in a person's blood pressure pattern, and the loss of nocturnal blood pressure reduction may pre-date the onset of clinical hypertension.

The anti-hypertensive effect of VL-PAG DBS has been observed in patients receiving treatment for neuropathic pain that were also diagnosed with hypertension (Green 2005) (Patel 2011). In one patient blood pressure could be increased or decreased acutely during surgery by stimulating either the dorsal or ventral PAG respectively. Chronic DBS of the VL-PAG caused a reduction in arterial pressure and analgesia which are associated with changes in heart rate variability indicative of inhibition of sympathetic vasomotor turn and increase in parasympathetic cardiac activity (Pereira 2010), which led the inventors to describe a "Method and Apparatus for Regulating Blood Pressure" WO 2007007058. Muscle sympathetic nerve activity was decreased in a patient during acute ventrolateral PAG DBS (Sverris Dottir 2014).

The inventors have observed striking responses in blood pressure reduction following DBS of the VL-PAG with acute complete normalisation of chronic hypertension from the impact which is usually not sustained beyond a few days to a week. Using a robot for stereotactic positioning of the electrode with visual image-based confirmation of the position of a pre-inserted guide tube and guide rod (Renishaw PLC) (Patel 2007), the inventors targeted the VL-PAG reliably and with precision. In 2011 (Neurology, 2011), the inventors reported the first case study where stimulation of the VL-PAG alleviated neuropathic pain and serendipitously produced a sustained (more than three years) normalisation of arterial pressure and that was not secondary to the relief from pain, as the patient's pain scores returned to pre-ventrolateral PAG stimulation levels after four months; and more recently in 2017 (Hypertension, 2017), the inventors reported the first case study where chronic and deep brain stimulation was able to decrease blood pressure and sympathetic nerve activity in a drug and device resistant severely hypertensive patient.

The Oxford Group had found in addition the depressor and bradycardic effect of acute VL-PAG DBS was coupled with an increase in baroreflex sensitivity, however in these cases the prevailing belief has been that the beneficial blood pressure effects were a secondary response to the relief of chronic pain.

In the inventor's experience, and consistent with spontaneous hypertensive rat studies where the VL-PAG is stereotactically targeted, that stimulation of the VL-PAG on its own is not sufficient for a persistent hypertensive response. Out of five cases that have been treated with hypertensive disease, with or without pain, two had failed to show a response. Close examination of the implanted lead positions and trajectories identified that the trajectories in the non-responders did not traverse along the lateral habenula and posterior commissure; and was 5-7 mm anterior (see FIG. 13). Both chronic non-responders had their distal electrodes in the VL-PAG; and both showed acute response, and likely related to the impact and swelling extending to the lateral habenula and posterior commissure, which on alleviation resulted in dissipation of response.

Vascular Dementia

Damage to blood vessels in the brain may come about as a result of a number of conditions including hypertension, heart disease, high cholesterol and diabetes. Vascular dementia can be caused by events that occur in cerebral blood vessels, firstly stroke and secondly small vessel disease. Vascular dementia resulting from stroke is categorised as either single infarct or multi infarct and depending on whether it was caused by one or several incidences of stroke. Small vessel disease results from damage to blood vessels that sit within the subcortical, deep and periventricular white matter and the lacunes of the central grey matter including thalamus and basal ganglia. Small vessel disease can be present in the absence of any cognitive impairment as well as varying levels of cognitive impairment ranging from mild cognitive impairment to dementia.

There is multiple experimental data illustrating the progression of vascular dementia caused by small vessel disease which tends to be continuous rather than step wise. In a study of patients with vascular dementia a decline of 4.5 MMSE points per year and was seen. Vascular dementia is associated with increase in mortality especially in the presence of white matter lesions and lacunar strokes. The presence of white matter lesions in patients with lacunar strokes is also a predictor of functional disability. A further study of patients with small vessel disease associated dementia and mild cognitive impairment resulted in 70% survival after 2.6 years and 50% survival after 4.3 years; and with the patients showing a drop of 3.9 points on a shortened MMSE scale. (Bennet H P and Corbett A J 2002 subcortical vascular disease and functional decline—a six year proedictor study. Journal of American Geriatrics Society 50 1969 to 1977; Frisoni G B et al 2002 mild cognitive impairment with subcortical vascular features—clinical characteristics and outcomes. 249, 1423-1432; Ballard C et al 2001 the progression of cognitive impairment and dementia with lewy bodies, vascular dementia and Alzheimer's disease. International Journal of Geriatric Psychiatry 16, 499 to 503.)

At North Bristol NHS Trust, two patients presenting with post-stroke pain secondary to hypertensive disease had deep brain stimulating leads implanted. Patient 1 had a previous history of up to six TIAs eventually culminating into a more significant right internal capsular, ventrolateral thalamic and insular stroke; and underwent implantation of a Medtronic 3387 lead (4×1.5 mm contacts separated by 1.5 mm intervals) into the VL-PAG. On further examination, the inventors found that proximal contacts lie adjacent to the posterior commissure and lateral habenula, and extend into the dorsomedial nucleus of the thalamus. With stimulation he only obtained pain response lasting three months, however his blood pressure remained controlled at two years (Patel et al, Neurology 2011).

Patient 2 had suffered up to ten stroke episodes resulting in hospitalisation. He had a Boston scientific 8 contact lead (8×1.5 mm contacts separated by 0.5 mm intervals) implanted across the dorsomedial nucleus of thalamus, lateral habenula, posterior commissure into the ventrolateral PAG. With low frequency stimulation across the VL-PAG, LH and PC, and high frequency stimulation across the DMN, his pain and his blood pressure are both controlled.

Patient 1 and Patient 2 now at 12 and five years' post-op, have suffered no further stroke events. With failure of pain control Patient 1 underwent implantation of bilateral dorsal anterior cingulate cortex leads in 2011; and for surgical planning he had the pre-existing lead removed and underwent MR imaging, which on comparison with the imaging from 2006 excluded any progression of small vessel disease, white matter lesions and lacunar strokes. Patient 2 has also shown stability of neuropsychometric testing at 5-years with no deterioration following the implantation and stimulation, and showed significant deterioration with transient stimulation cessation.

Epilepsy

Epileptic seizures result from excessive and uncontrolled desynchronisation of cortical nerve brain electrical activity, occurring in approximately 1% of the world population, and are controllable with medication only in about 70% of cases. In the remaining 30% surgical therapies are required, where neuromodulation techniques are becoming emerging treatment options, specifically as they enable changes in brain activity of a controlled manner whilst the effects are reversible unlike those of lesioning techniques.

Bilateral anterior nucleus of the thalamus high frequency deep brain stimulation has been shown to progressively reduce seizure frequency and severity especially in those with generalised tonic clonic seizures where there is no surgically amenable target. This has been shown as part of the SANTE and MORE studies conducted by Medtronic Inc. In patients with medically refractory partial and secondarily generalised seizures, bilateral stimulation of the anterior nucleus has been demonstrated to reduce seizures by more than 70% over a seven year period (SANTE trial).

In two cases where deep brain stimulating systems were implanted for hypertension, both patients had a longstanding history off associated seizures. The deep brain stimulating systems were implanted across the right medial thalamus into the VL-PAG. With combined low frequency stimulation across the ventrolateral periaqueductal gray, periventricular gray, posterior commissure and habenula and in combination high frequency stimulation of the (along the top extent of the lead) parafascicular thalamic and dorsomedial thalamic nuclei, both patients had complete alleviation of seizure activity. Cerebral blood flow studies in the second patient with stimulation on and off identified a 39.5% increase in cerebral blood flow, a 16.7% increase in cerebral blood volume and a 12.5% reduction in mean transit time, as shown on CT perfusion.

Cerebral vasoconstriction and reduction in cerebral blood flow have been postulated to be a prodromal event to seizure or ictal activity, while studies have identified generalised increase in cerebral blood flow following a seizure in anticipation restoring cerebral blood flow; and peri-ictal hypotension is well identified in patients with epilepsy and accounts for cardiovascular collapse and that may lead to sudden unexpected death in epilepsy (SUDEP), which interestingly is more common nocturnally and consistent with the loss of diurnal rhythm commonly seen in chronic hypertensive disease.

The DBS lead with electrode span extending from the anterior nucleus of the thalamus down to the ventrolateral periaqueductal gray is implanted through a transventricular trajectory with appropriate collision avoidance of vasculature. The contacts extend from the anterior nucleus of the thalamus across the dorsomedial nucleus of the thalamus, the parafascicular nucleus of the thalamus adjacent to the lateral habenula, the periventricular gray adjacent to the posterior commissure and into the ventrolateral periaqueductal gray.

Whilst the anterior nucleus of the thalamus has been established for the treatment of generalised seizures, efficacy has also been seen with bilateral centromedian—parafascicular nucleus stimulation. Stimulation of the periaqueductal gray has been shown in animal models to eliminate the cortical rhythm asynchrony; and lends itself as an adjuvant candidate cerebral rhythm stabilisation and seizure control.

Cerebral Glioma Disease

Iodine-123 labelled hydroxy-iodo-propyl-diamine (HIPDm) is a diffusible indicator with an 85 to 90% extraction fraction and stable retention in the brain for more than two hours, and with SPECT (single photon emission computed tomographic) scan, it has been shown that HIPDm distribution occurs in proportion to regional cerebral blood flow. Consistently there is a prominent decrease in HIPDm accumulation and calculated cerebral blood flow with cerebral infarction in the distribution of middle cerebral artery ligation. Interestingly, patients with glioma disease have been shown to have diminished HIPDm accumulation due to decreased cerebral blood flow in the region of the neoplasm, and also associated in the surrounding regions where there is vasogenic oedema and within the overlying grey matter.

Enhancing cerebral blood flow is likely to benefit combating a lesion through the body's own immune system, and through enhanced delivery of chemotherapeutic and immunotherapy enhanced immunoglobulins and leucocytes to combat this diffuse disease. Accordingly, neurostimulation techniques described herein may be used to enhance cerebral blood flow in order to treat cerebral glioma disease.

Psychosis, Depression and Schizophrenia

Dysfunctions of the habenulae have been implicated in psychosis including depression, schizophrenia and drug-induced psychosis (Sandyk, 1991-Scheibel, 1997). In rat models of depression the regional glucose metabolism is elevated in the lateral habenula more consistently than any other brain area (Caldecott-Hazard et al, 1988). Transient depressive relapses in volunteer patients by rapidly depleting plasma tryptophan, the precursor of serotonin (5-HT), are associated with correlated increases in activity in habenula and the dorsal raphe as the rate of depressed mood increases (Morris et al, 1999).

In patients with chronic schizophrenia calcification of the habenula occurs much more frequently than in age match controls (Sandyk, 1992; Caputo et al, 1998). The influenza virus, which increases the risk of schizophrenia if experienced prenatally, selectively damages the habenula when introduced into the brain via the olfactory bulb (Mori et al, 1999). Refractory schizophrenia remains a major unsolved clinical problem, with 10 to 30% of patients not responding to standard treatment options. Similarly, at Southmead Hospital, a 70-year-old gentleman who two years previously had been diagnosed with late onset psychosis, was now identified with a central lymphoma affecting the habenula.

The inventors have found that high amplitude low frequency stimulation of the habenula in one patient has resulted in intensification of both auditory and visual hallucinations. The latter relates to a 58-year-old lady who having presented with post-surgical trigeminal anaesthesia dolorosa, in 2010 (age 49) underwent implantation of right sided deep brain stimulating leads into the ventrolateral periaqueductal gray and parafascicular nucleus. Stimulation of the ventrolateral periaqueductal gray in combination with high frequency stimulation of the medial thalamus (dorsomedial nucleus), resulted in some progression of longstanding confusion between thoughts and conversations from 2012 to 2017, in combination with auditory and at times visual hallucinations. Cessation of stimulation for four days resulted in complete alleviation of the confusion and hallucinations, whilst the pain severely exacerbated. Stimulation reprogramming with left medial thalamus (reduction in amplitude), in combination with high-frequency stimulation of the proximal ventrolateral PAG lead spanning across the lateral habenula, resulted in complete alleviation of the visual hallucinations and 50% reduction of confusion and auditory hallucinations, whilst her facial pain remained under control as before. So, combined high frequency stimulation of the DMN and low frequency stimulation of the VL-PAG resulted in cognitive disturbance and hallucinations, likely as a result of inhibition of the lateral habenula. High frequency stimulation to the DMN and combined with low frequency stimulation of the LH resulted in improvement of the cognitive disturbance and psychosis. Further amplitude reduction within the DMN resulted in cumulative improvement of the cognitive and psychosis disturbance, whilst pain control diminished. Combined high frequency stimulation of the DMN, with low frequency stimulation spanning from the LH to the VL-PAG, may optimise pain, mood, cognitive and psychosis control.

Renal Failure

Consistent with the dorsal PAG eliciting a fight or flight response and the VL-PAG eliciting a freezing response, stimulation of the dorsal PAG can invariably induce marked reduction of glomerular filtration rate (GFR) with sustained effect likely to provoke acute renal failure, whereas a stimulation of the VL-PAG improves GFR and helps alleviate acute renal failure.

The inventors have found that when low frequency stimulation across the lateral habenula into the VL-PAG is combined with high frequency stimulation of the DMN and/or the DACC, progressive normalisation of GFR can be effected, and deterioration prevented; this is likely a result of reversal of an autonomic imbalance. Accordingly, this lends itself to the use of stimulation for the treatment of renal failure, and especially in pre-dialysis patients where this combined stimulation paradigm can be utilised to minimise progression, potentially promotes recovery and prevents the need for dialysis.

Autoregulation of Cerebral Blood Flow

Autoregulation of cerebral blood flow is the ability of the brain to maintain relatively constant blood flow despite changes in perfusion pressure. Autoregulation is present in many vascular beds but is particularly well developed in the brain, likely due to the need for a constant blood supply and water homeostasis. In normotensive adults cerebral blood flow is maintained at about 50 ml per 100 grams of brain tissue per minute, provided cerebral perfusion pressure is in the range of 60 to 160 mmHg. Above and below this limit autoregulation is lost and cerebral blood flow becomes dependent on mean arterial pressure in a linear fashion. When cerebral perfusion pressure falls below the lower limit of autoregulation, cerebral ischaemia ensues. The reduction in cerebral blood flow is compensated for by an increase in oxygen extraction from the blood.

Cerebral autoregulation aims to stabilise the blood flow to the brain during variations in perfusion pressure, thus protecting the brain against the risks of low and high systemic blood pressure. This vital mechanism is severely impaired in the transgenic mouse model of Alzheimer's disease that abundantly produces amyloid beta peptide beta 1 to 42. Experiments reveal that total cerebral blood flow is 20% lower in Alzheimer's disease patients in comparison to age matched non-demented controls (Roher A E et al Cerebral Blood Flow in Alzheimer's Disease, Vascular Health and Risk Management 2012 Volume 8 pages 599 to 611). The presence of small vessel disease, lacunar infarcts and strokes may prompt the onset of dementia or worsen the clinical course of Alzheimer's disease, clearly demonstrating that deficiencies in cerebral blood flow are involved in the global pathogenesis of cognitive decline. In older adults, chronic hypoperfusion caused by lower cardiac output has been correlated with white matter hyperintensities and abnormal brain ageing. In Alzheimer's disease, patients' systolic and pulse pressure are diminished. The blood flow decrease in the brain ideally needs to be compensated by an increase in cardiac output which elevates systolic blood pressure to maintain adequate brain perfusion, however the low blood pressures alter in chronic progressive disease.

Cerebrovascular disease and Alzheimer's disease in the elderly may have a number of causal relationships. The association of thromboembolic disease and multi-infarct or vascular dementia with Alzheimer's disease is well recognised. Destruction of the smooth muscle cells in the leptomeningeal and intracerebral arteries in cerebral amyloid angiopathy may not only predispose to intracerebral haemorrhage, but may also have an effect on cerebral blood flow and autoregulation. Cerebral amyloid angiopathy impedes the drainage of interstitial fluid and peptides such as soluble Abeta from the brain; and accordingly strategies for facilitating the drainage of Abeta along perivascular pathways may strongly benefit future therapeutic interventions in patients with Alzheimer's disease. In particular measures to increase cerebral blood flow in combination with drugs and molecules administered to enhance fibrinolysis and solubility of Abeta are likely to be highly beneficial in the treatment of Alzheimer's disease.

In cognitively normal elderly individuals, white matter hyperintensities (WMH) are commonly viewed as a marker of cerebral small vessel disease (SVD). SVD is due to exposure to systemic vascular injury processes associated with highly prevalent vascular risk factors such as hypertension, high cholesterol and diabetes. However cerebral amyloid accumulation is also prevalent in this population and is associated with WMH accrual. It has been shown that greater amyloid burden and a history of hypertension are independently associated with greater WMH volume Autoregulation may or may not be impaired in patients with significant disease of the cerebral arteries; moreover, autoregulatory capacity may be partly or completely lost with Alzheimer's disease, vascular dementia, brain multiple small vessel disease or infarctions, progressive multiple sclerosis, traumatic brain disease and vasospastic disease following subarachnoid haemorrhage.

In subjects with minimal conscious state, arterial spin labelling has identified globally decreased serum blood flow and a selective reduction of serum blood flow within the medial pre-frontal and mid-frontal cortical regions as well as the grey matter (Liu et al Neurology 2011 Volume 77 No 16 Pages 1518-1523).

Neurostimulation techniques described herein may be used to enhance and regulate cerebral blood flow in order to treat conditions associated with disturbances in autoregulation or reduced cerebral blood flow. In particular, by using one or more physiological parameters of the subject (e.g. cerebral blood flow, intracranial pressure, blood pressure, etc.) as feedback for controlling the neurostimulation, it may be possible to accurately regulate and control the subject's cerebral blood flow.

Conditions where there is documented reduced cerebral blood flow and autoregulation disturbance include resistant hypertension, ischaemic stroke, haemorrhagic stroke, traumatic brain injury, vasospasm, subarachnoid haemorrhage, minimally conscious state, vascular dementia, Alzheimer's disease, multiple sclerosis, depression, schizophrenia and migraine with aura.

Autonomic Dysfunction

Conditions associated with autonomic dysfunction include alcoholism, amyloidosis, cerebral infarcts, diabetes mellitus, Huntington's disease, multiple sclerosis, multiple system atrophy, Parkinson's disease, Alzheimer's disease, Toxic neuropathies, brain tumours.

In conditions associated with autonomic dysfunction, there is autonomic dysfunction or imbalance with increased sympathetic activity and reduced parasympathetic activity. With a combined neurostimulation of targets in the brain at appropriate prescription, deep brain stimulation may reverse this imbalance and reinstate normal autonomic function which is integral to enhancing cerebral blood flow, re-establishing the circadian rhythm and treating the conditions.

Circadian Rhythms and Sleep:

Many characteristics of human behaviour and their underlying molecular biochemical processes are driven by circadian rhythms. Disruptions of circadian rhythms are being increasingly connected to numerous clinical conditions, and include metabolic syndrome and obesity, premature aging, diabetes, immune deficiencies, cardiac arrhythmias, cardiovascular disease, hypertension and cancers. Sleep and circadian rhythm disruption is a common feature of Alzheimer's disease, dementias and other neurodegenerative diseases; and schizophrenia, depression and other psychiatric disease.

Emerging data suggests that re-instatement of circadian rhythms, sleep and chronobiology, might prove very important in the treatment of disease states. There is good evidence that sleep function is critical for memory consolidation, and it is becoming increasingly that it is also required for effective removal of waste from the brain through the brain glymphatic and lymphatic systems, and with this important implications for the treatment of Alzheimer's disease, dementias and other neurodegenerative diseases.

Brain Coherence and Synchronization:

The hypothesis "communication through coherence" is now widely accepted, such that anatomic communications can become effective or inefficient owing to the presence or lack of rhythmic synchronization respectively. It is known that communication between selective brain structures as well as oscillatory activity in them can violate in neurological (e.g. epilepsy), neurodegenerative (e.g. Alzheimer's disease) and psychiatric (e.g. schizophrenia) disorders. There is accumulating evidence indicating that coupling between the phase of slow oscillations (especially in the theta frequency 4-12 Hz range) and the amplitude of fast oscillations (gamma 30 to 100 Hz range) are involved in information processing, and disruptions of this theta and gamma rhythm coherence is seen in disease.

Clauses

The invention is described in the following clauses:

1. A method of treatment performed on a subject's brain, the method including a step of applying one or more neuromodulation signals to the lateral habenula and the posterior commissure.

2. A method according to clause 1, further including applying one or more neuromodulation signals to one or more additional targets in the subject's brain.

3. A method according to clause 2, wherein the one or more additional targets include the dorsomedial nucleus of the thalamus.

4. A method according to clause 3, wherein a first neuromodulation signal having a first frequency is applied to the dorsomedial nucleus, and one or more second neuromodulation signals are applied to the lateral habenula and the posterior commissure, wherein each of the one or more second neuromodulation signals has a frequency lower than the first frequency.

5. A method according to clause 4, wherein the first frequency is greater than 70 Hz, and each of the one or more second neuromodulation signals has a frequency between 4 and 50 Hz.

6. A method according to one of clauses 2 to 5, wherein the one or more additional targets include the ventrolateral periaqueductal gray, VL-PAG.

7. A method according to clause 6 as dependent on clause 4 or 5, wherein the one or more second neuromodulation signals are applied to the lateral habenula, the posterior commissure and the VL-PAG.

8. A method according to any preceding clause, further including:

identifying a trajectory in the subject's brain, the trajectory linking the dorsomedial nucleus and the VL-PAG across the lateral habenula and the posterior commissure; and implanting an electrode lead into the subject's brain along the identified trajectory, the electrode lead including a plurality of electrodes for applying the one or more neuromodulation signals.

9. A method according to clause 8, wherein the trajectory is such that a spacing between the electrode lead and the lateral habenula is less than 5 mm, and/or a spacing between the electrode lead and the posterior commissure is less than 5 mm.

10. A method according to any preceding clause, further including applying a neuromodulation signal to the dorsal anterior cingulate cortex and/or the corpus callosum.

11. A method according to clause 10 as dependent on clause 8 or 9, wherein the trajectory further passes adjacent the dorsal anterior cingulate cortex and the electrode lead includes an electrode arranged to apply the neuromodulation signal to the dorsal anterior cingulate cortex; and/or the trajectory further passes adjacent the corpus callosum and the electrode lead includes an electrode arranged to apply the neuromodulation signal to the corpus callosum.

12. A method according to clause 10 as dependent clause 8 or 9, further including implanting a second electrode lead into the subject's brain, the second electrode lead including an electrode arranged to apply the neuromodulation signal to the dorsal anterior cingulate cortex and/or the corpus callosum.

13. A method according to any preceding clause, further including detecting a physiological parameter of the subject, and adjusting at least one of the one or more neuromodulation signals based on the detected physiological parameter.

14. A method according to any preceding clause, further including adjusting at least one of the one or more neuromodulation signals based on the subject's circadian rhythm.

15. A method according to any preceding clause, further including applying a stimulation signal to a carotid body and/or a carotid baroreceptor in the subject.

16. A method according to any preceding clause, wherein the method is for treating one or more of hypertension, a traumatic brain injury, cerebral vasospasm, cerebral infarction, a brain tumour, cerebral glioma, Parkinson's disease, Alzheimer's disease, vascular dementia, amyotrophic lateral sclerosis, Huntington's disease, multiple system atrophy, multiple sclerosis, addiction, depression, schizophrenia, obesity, renal failure, epilepsy and attention deficit hyperactivity disorder.

17. An apparatus for performing a treatment on a subject's brain, the apparatus comprising an electrode lead arranged for insertion into the subject's brain, a distal portion of the electrode lead having a plurality of electrodes arranged to apply one or more neuromodulation signals to the lateral habenula and the posterior commissure of the subject's brain; and a controller configured to generate the one or more neuromodulation signals applied by the plurality of electrodes.

18. An apparatus according to clause 17, wherein the plurality of electrodes is further arranged to apply one or more neuromodulation signals to one or more additional targets in the subject's brain.

19. An apparatus according to clause 18, wherein the one or more additional targets include the dorsomedial nucleus of the thalamus.

20. An apparatus according to clause 18 or 19, wherein the one or more additional targets include the VL-PAG.

21. An apparatus according to one of clauses 17 to 20, wherein the plurality of electrodes are evenly spaced in a longitudinal direction along a length of the distal portion of the electrode lead.

22. An apparatus according to clause 21, wherein the plurality of electrodes spans a length between 20-25 mm.

23. An apparatus according to one of clauses 17 to 22, further including a proximal electrode arranged to apply a neuromodulation signal to the dorsal anterior cingulate and/or the corpus callosum.

24. An apparatus according to clause 23, wherein the proximal electrode comprises a proximal electrode disposed on the electrode lead.

25. An apparatus according to clause 24, wherein a length of the proximal electrode disposed on the electrode lead is greater than a length of each of the electrodes in the plurality of electrodes.

26. An apparatus according to clause 25, wherein the length of the proximal electrode disposed on the electrode lead is between 10-30 mm.

27. An apparatus according to one of clauses 17 to 26, further comprising a guide tube for insertion into the subject's brain, the guide tube including a hollow tube defining a longitudinal channel in which the electrode lead is receivable.

28. An apparatus according to clause 27 as dependent on one of clauses 24 to 26, wherein the guide tube includes a window formed in a sidewall of the hollow tube, the window being arranged to expose the proximal electrode disposed on the electrode lead to the outside of the hollow tube when the electrode lead is received in the longitudinal channel of the hollow tube.

29. An apparatus according to clause 28, wherein a length of the window is shorter than a length of the proximal electrode disposed on the electrode lead.

30. An apparatus according to clause 28 or 29, wherein the guide tube includes a marker for indicating a direction in which the window is facing.

31. An apparatus according to one of clauses 28 to 30, wherein the window comprises two or more apertures in the sidewall of the hollow tube.

32. An apparatus according to clause 27 as dependent on one of clauses 24 to 26, wherein the proximal electrode comprises an outer electrode at an outer surface of the hollow tube, and the outer electrode is arranged for electrical connection to the proximal electrode disposed on the electrode lead when the electrode lead is received in the longitudinal channel of the hollow tube.

33. An apparatus according to clause 27 as dependent on clause 23, wherein the proximal electrode comprises an outer electrode at an outer surface of the hollow tube, and the outer electrode is electrically connected to the controller via a connecting lead extending through the hollow tube.

34. An apparatus according to one of clauses 27 to 33, wherein the guide tube further comprises a cap that is securable to a hole in the subject's skull, the cap including a passageway through which the hollow tube is insertable to insert the hollow tube into the subject's brain.

35. An apparatus according to clause 34, further comprising a first limiter secured to a proximal portion of the hollow tube, the first limiter being arranged to abut against the cap when a pre-determined length of the hollow tube is inserted through the passageway.

36. An apparatus according to one of clauses 27 to 35, further comprising a second limiter, the second limiter being secured to a proximal portion of the electrode lead, and arranged to abut against a proximal end of the guide tube when a pre-determined length of the electrode lead protrudes from the distal opening of the hollow tube.

37. An apparatus according to one of clauses 17 to 36, further comprising a sensor arranged to detect a physiological parameter of the subject and to generate an output signal related to the detected physiological parameter, wherein the controller is configured to adjust at least one of the one or more neuromodulation signals based on the output signal from the sensor.

38. An apparatus according to one of clauses 17 to 37, further comprising an external power supply, wherein the external power supply includes a transmitter for wirelessly transmitting power to the controller.

39. An apparatus according to clause 38, further including a wearable cap configured to hold the transmitter in proximity of the controller.

40. An apparatus according to one of clauses 17 to 39, further including one or more stimulation electrodes for applying one or more stimulation signals to a carotid body and/or a carotid baroreceptor in the subject.

41. An apparatus according to clause 40, wherein the controller is further configured to generate the stimulation signal.

42. A guide tube for insertion into a subject's brain, the guide tube comprising a hollow tube defining a longitudinal channel in which an electrode lead is receivable;
wherein the guide tube includes a window formed in a sidewall of the hollow tube, the window being arranged to expose a proximal electrode on the electrode lead to an outside of the hollow tube when the electrode lead is received in the longitudinal channel of the hollow tube.

43. A guide tube according to clause 42, wherein the guide tube includes a marker for indicating a direction in which the window is facing.

44. A guide tube according to clause 42 or 43, wherein the window comprises two or more apertures in the sidewall of the hollow tube.

45. A guide tube for insertion into a subject's brain, the guide tube comprising a hollow tube defining a longitudinal channel in which an electrode lead is receivable;
wherein the guide tube includes an outer electrode on an outer surface of the hollow tube.

46. A guide tube according to clause 45, further comprising a connecting lead extending through the hollow tube for connecting the outer electrode to a controller.

47. A guide tube according to clause 45, wherein the outer electrode is configured for electrical connection to a proximal electrode on the electrode lead when the electrode lead is received in the longitudinal channel of the hollow tube.

48. A guide tube according to one of clauses 42 to 47, further comprising a cap that is securable to a hole in the subject's skull, the cap including a passageway through which the hollow tube is insertable to insert the hollow tube into the subject's brain.

49. A guide tube according to clause 48, further comprising a first limiter secured to a proximal portion of the hollow tube, the first limiter being arranged to abut against the cap when a pre-determined length of the hollow tube is inserted through the passageway.

50. A method of treatment performed on a subject, the method including:
applying one or more neuromodulation signals to one or more targets in the subject's brain; and
applying a stimulation signal to a carotid body and/or a carotid baroreceptor in the subject.

51. A system comprising:
an apparatus for applying one or more neuromodulation signals to one or more targets in the subject's brain; and
a stimulation electrode for applying a stimulation signal to a carotid body and/or a carotid baroreceptor in the subject.

The invention claimed is:

1. A method of treatment performed on a subject's brain, the method comprising:
    a step of applying one or more neuromodulation signals to the lateral habenula and the posterior commissure;
    applying one or more neuromodulation signals to one or more additional targets in the subject's brain, wherein the one or more additional targets include the dorsomedial nucleus of the thalamus;
    wherein a first neuromodulation signal having a first frequency is applied to the dorsomedial nucleus, and one or more second neuromodulation signals are applied to the lateral habenula and the posterior commissure, wherein each of the one or more second neuromodulation signals has a frequency lower than the first frequency.

2. A method according to claim 1, wherein the first frequency is greater than 70 Hz, and each of the one or more second neuromodulation signals has a frequency between 4 and 50 Hz.

3. A method according to claim 1, wherein the one or more additional targets include the ventrolateral periaqueductal gray, VL-PAG.

4. A method according to claim 1, wherein the one or more second neuromodulation signals are applied to the lateral habenula, the posterior commissure and the ventrolateral periaqueductal gray, VL-PAG.

5. A method according to claim 1, further including applying a neuromodulation signal to the dorsal anterior cingulate cortex and/or the corpus callosum.

6. A method according to claim 1, further including detecting a physiological parameter of the subject, and adjusting at least one of the one or more neuromodulation signals based on the detected physiological parameter.

7. A method according to claim 1, further including adjusting at least one of the one or more neuromodulation signals based on the subject's circadian rhythm.

8. A method according to claim 1, further including applying a stimulation signal to one of a carotid body or a carotid baroreceptor in the subject.

9. A method according to claim 1, wherein the method is for treating one or more of hypertension, a traumatic brain injury, cerebral vasospasm, cerebral infarction, a brain tumour, cerebral glioma, Parkinson's disease, Alzheimer's disease, vascular dementia, amyotrophic lateral sclerosis, Huntington's disease, multiple system atrophy, multiple sclerosis, addiction, depression, schizophrenia, obesity, renal failure, epilepsy and attention deficit hyperactivity disorder.

10. A method of treatment performed on a subject's brain, the method comprising:
    identifying a trajectory in the subject's brain, the trajectory linking the dorsomedial nucleus and the ventrolateral periaqueductal gray, VL-PAG across the lateral habenula and the posterior commissure;
    implanting an electrode lead into the subject's brain along the identified trajectory, the electrode lead including a plurality of electrodes for applying the one or more neuromodulation signals; and
    applying one or more neuromodulation signals to the lateral habenula and the posterior commissure.

11. A method according to claim 10, wherein the trajectory is such that a spacing between the electrode lead and the lateral habenula is less than 5 mm, and/or a spacing between the electrode lead and the posterior commissure is less than 5 mm.

12. A method according to claim 10, wherein the trajectory further passes adjacent to one of the dorsal anterior cingulate cortex wherein the electrode lead includes an electrode arranged to apply the neuromodulation signal to the dorsal anterior cingulate cortex or the corpus callosum wherein the electrode lead includes an electrode arranged to apply the neuromodulation signal to the corpus callosum.

13. A method according to claim 10, further including implanting a second electrode lead into the subject's brain, the second electrode lead including an electrode arranged to apply the neuromodulation signal to one of the dorsal anterior cingulate cortex or the corpus callosum.

* * * * *